United States Patent
Callas et al.

(10) Patent No.: US 8,034,098 B1
(45) Date of Patent: Oct. 11, 2011

(54) VALVE ANNULUS CONSTRICTION APPARATUS AND METHOD

(75) Inventors: Peter L. Callas, Redwood City, CA (US); Richard J. Saunders, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 46 days.

(21) Appl. No.: 11/536,060

(22) Filed: Sep. 28, 2006

Related U.S. Application Data

(63) Continuation of application No. 10/295,323, filed on Nov. 15, 2002, now abandoned.

(51) Int. Cl.
*A61F 2/82* (2006.01)

(52) U.S. Cl. ........................................ 623/1.15

(58) Field of Classification Search ........ 623/1.14–1.16, 623/1.2, 1.24, 1.36, 2.36, 2.38, 903, 904; 606/200
See application file for complete search history.

(56) References Cited

U.S. PATENT DOCUMENTS

| | | | |
|---|---|---|---|
| 5,383,892 A | 1/1995 | Cardon et al. | |
| 5,817,126 A | 10/1998 | Imran | |
| 5,855,600 A | 1/1999 | Alt | |
| 5,961,440 A | 10/1999 | Schweich, Jr. et al. | |
| 6,001,127 A | 12/1999 | Schoon et al. | |
| 6,045,497 A | 4/2000 | Schweich, Jr. et al. | |
| 6,048,350 A * | 4/2000 | Vrba | 623/1.11 |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,110,100 A | 8/2000 | Talpade | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,183,411 B1 | 2/2001 | Mortier et al. | |
| 6,187,034 B1 * | 2/2001 | Frantzen | 623/1.11 |
| 6,231,587 B1 | 5/2001 | Makower | |
| 6,258,117 B1 * | 7/2001 | Camrud et al. | 623/1.16 |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,402,781 B1 | 6/2002 | Langberg et al. | |
| 6,585,758 B1 | 7/2003 | Chouinard et al. | |
| 6,810,882 B2 | 11/2004 | Langberg et al. | |
| 6,945,994 B2 | 9/2005 | Austin et al. | |
| 2001/0018611 A1 * | 8/2001 | Solem et al. | 623/2.37 |
| 2001/0044568 A1 | 11/2001 | Langberg et al. | |
| 2002/0016628 A1 | 2/2002 | Langberg et al. | |
| 2002/0035361 A1 | 3/2002 | Houser et al. | |
| 2002/0087173 A1 | 7/2002 | Alferness et al. | |

(Continued)

FOREIGN PATENT DOCUMENTS

WO   WO 98/29041   7/1998

(Continued)

*Primary Examiner* — Ryan Severson
(74) *Attorney, Agent, or Firm* — Jonathan Feuchtwang; Blakely Sokoloff Taylor & Zafman, LLP

(57) ABSTRACT

An apparatus is described for supporting and/or constricting a surface of a valve annulus. The apparatus includes a tubular member of dimensions suitable for insertion into a body vessel. The tubular member includes at least two first segments attachable to an interior wall of the body vessel. The tubular member further includes at least one second segment which is capable of decreasing its axial length to draw one of the first segments towards the other first segment.

27 Claims, 22 Drawing Sheets

U.S. PATENT DOCUMENTS

| | | |
|---|---|---|
| 2002/0103532 A1 | 8/2002 | Langberg et al. |
| 2002/0103533 A1 | 8/2002 | Langberg et al. |
| 2002/0198588 A1 | 12/2002 | Armstrong et al. |

FOREIGN PATENT DOCUMENTS

| | | |
|---|---|---|
| WO | WO 99/30647 | 6/1999 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/28455 A1 | 4/2001 |
| WO | WO 01/54618 A1 | 8/2001 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |

* cited by examiner

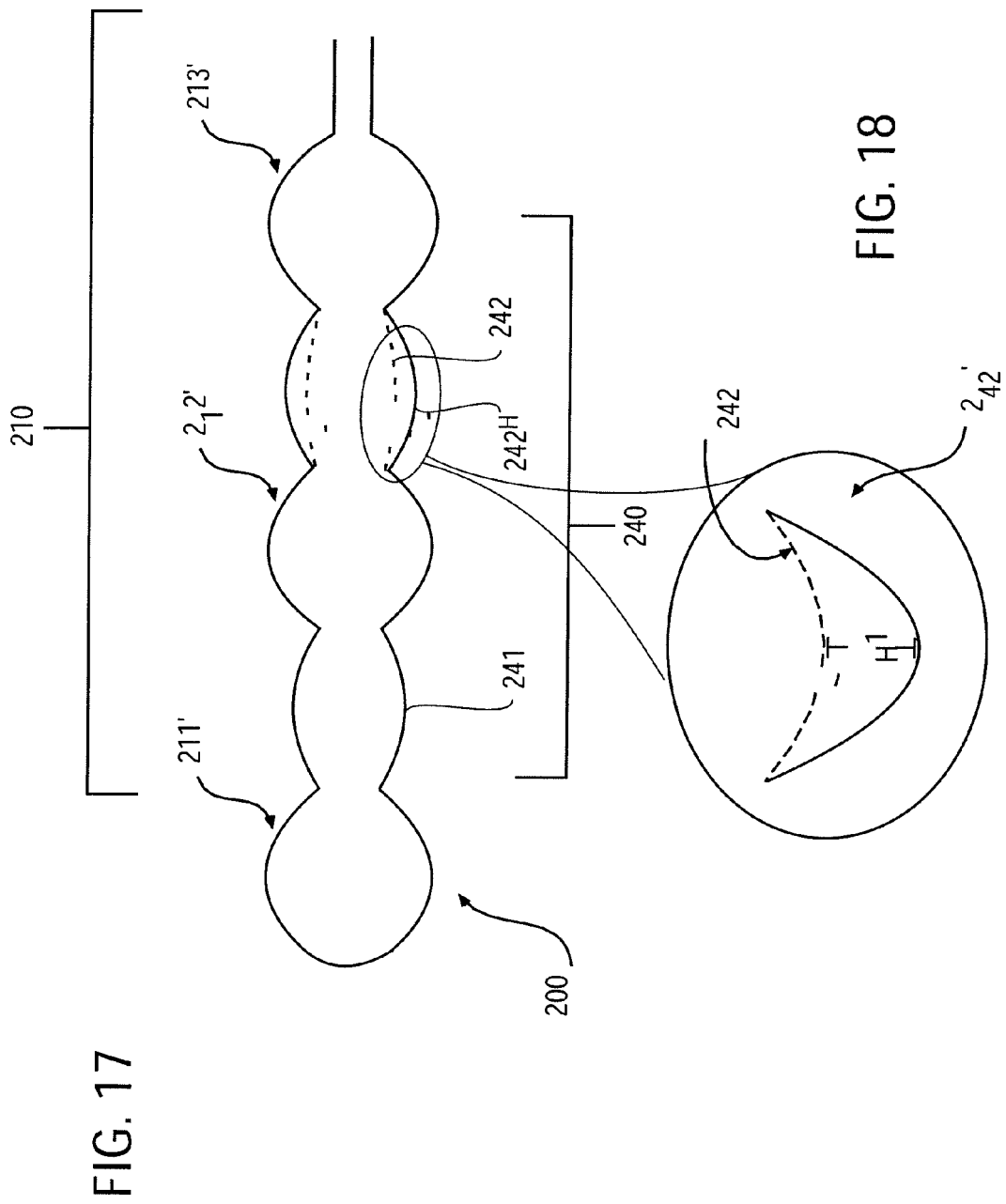

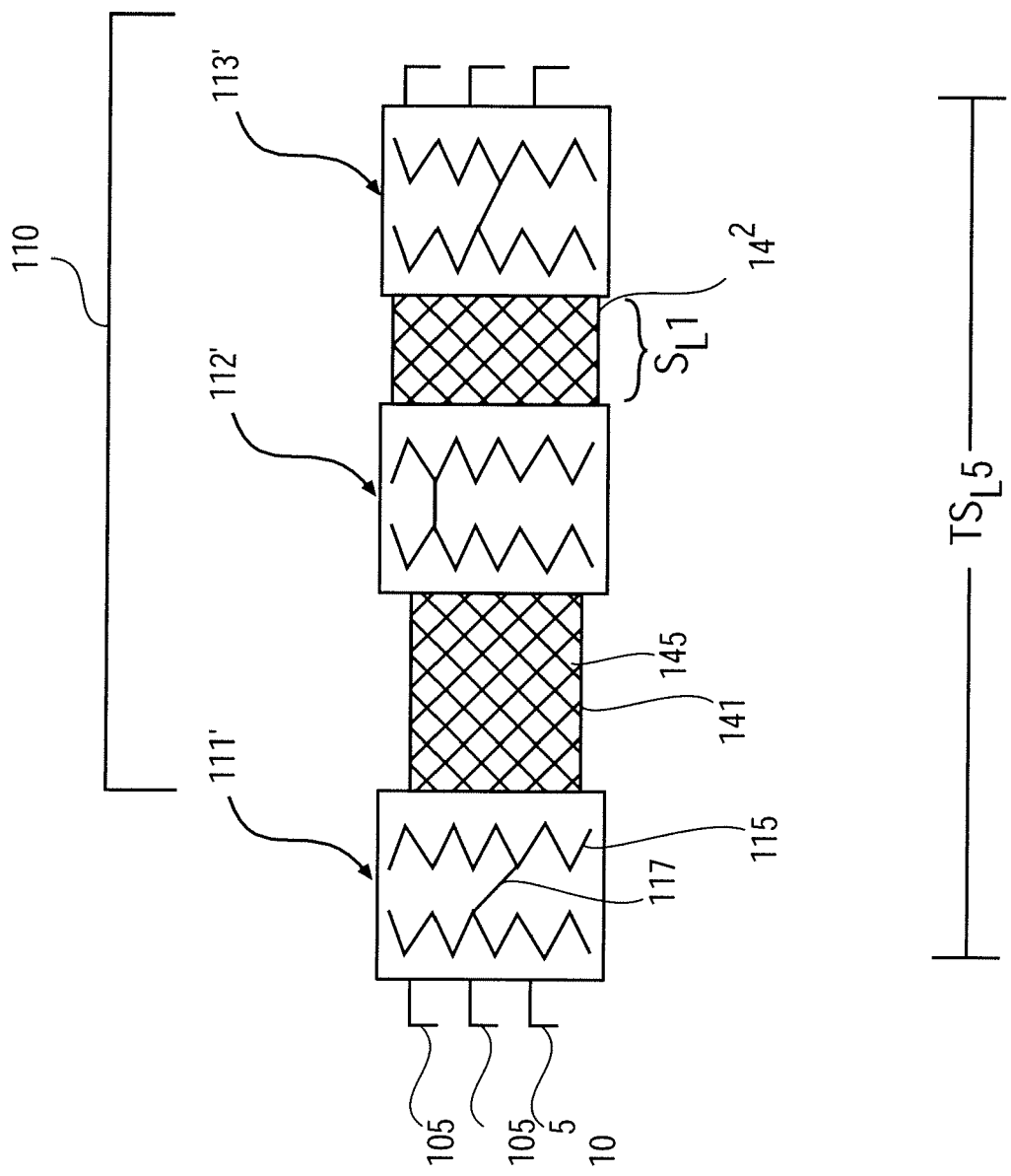

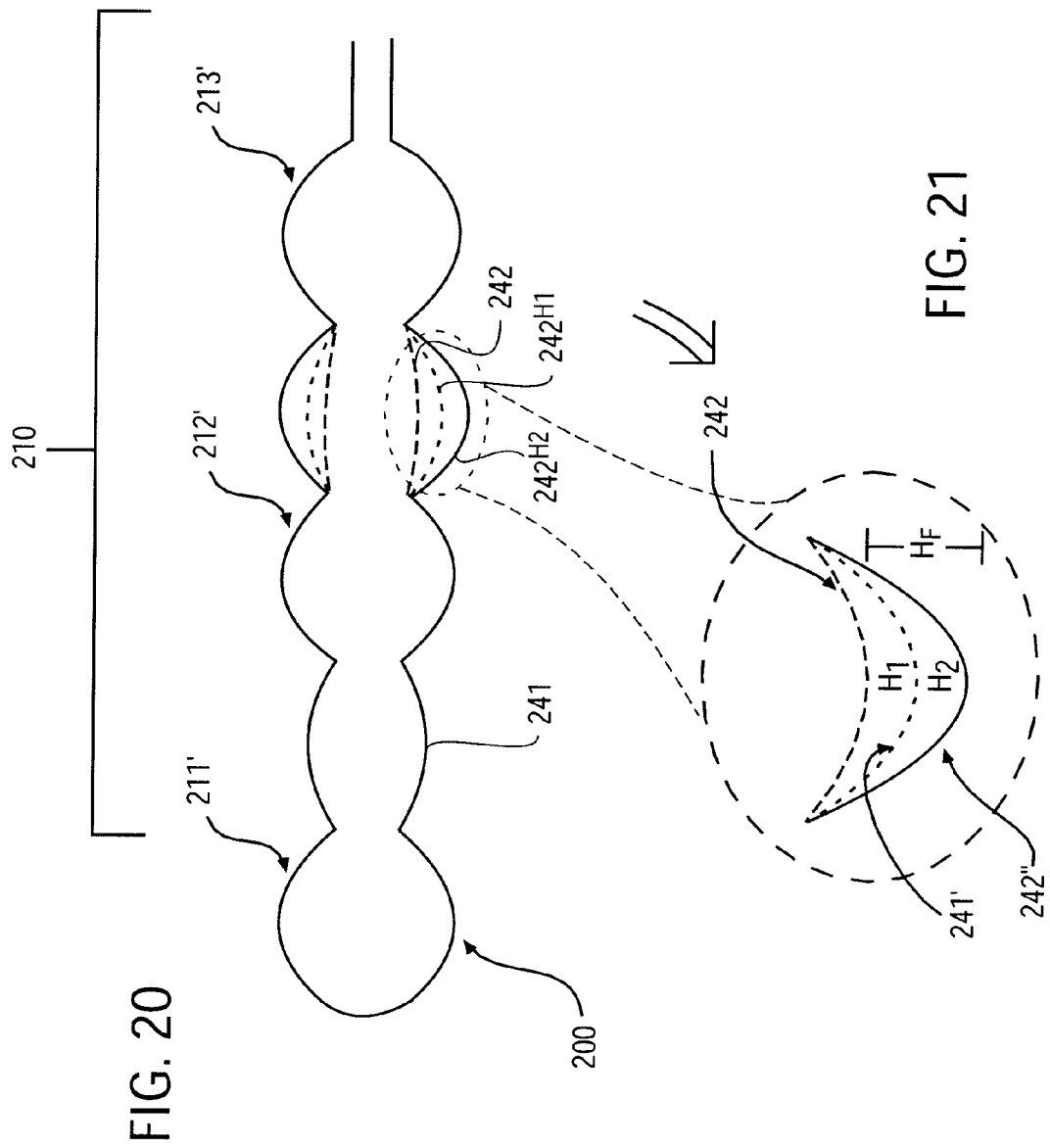

VALVE ANNULUS CONSTRICTION APPARATUS AND METHOD

CROSS-REFERENCE TO RELATED APPLICATION

This application is a continuation of application Ser. No. 10/295,323, filed Nov. 15, 2002 now abandoned.

BACKGROUND

1. Field

Stent like structures for insertion into body vessels, and the treatment of valve insufficiency.

2. Background

Generally speaking, oxygenated blood travels from the lungs to the left atrium by way of the pulmonary veins. The veins from the systemic circuit, the venae cavae and coronary sinus carry blood deficient in oxygen into the right atrium. The right ventricle takes blood received from the right atrium and sends it to the lungs, while the left ventricle takes blood received from the left atrium and sends it to the aorta.

The atrioventricular valves between respective ones of the atria and ventricles play important roles in the transport of blood through the body. The atrioventricular valves open during diastole, when the heart muscle relaxes, to allow blood to flow from the atria into the ventricles. The atrioventricular valves close during systole, when the heart muscle contracts, preventing the back flow of blood into the atria and allowing blood from the ventricles to be efficiently pumped into the lungs via the pulmonary tract and to the rest of the body via the aorta.

The mitral valve is the atrioventricular valve that controls blood flow from the left atrium into the left ventricle. The mitral valve is a bicuspid valve, describing the two cusps or leaflets that open and close the valve. The cusps or leaflets are attached to a muscular and fibrous ring around the orifice (mitral valve annulus) and their apices hang down into the left ventricle. When the ventricle fills with blood and begins to contract, the valve cusps or leaflets flow into position in the atrioventricular opening and are forced shut (coaptate) by the increasing pressure. To prevent the valve cusps or leaflets from turning into the left atrium and regurgitating blood, tendinous cords, the chordae tendineae, are attached to the free margins and ventricular surfaces of the cusps or leaflets. At the other ends, these cords attached to one of a respective pair of papillary muscles projecting from the ventricular wall. By contracting, these muscles maintain the integrity of the valve during ventricular contraction or systole.

When the two cusps or leaflets of the mitral valve do not completely close, there is backflow, or regurgitation of blood. The backflow increases the pressure in the left atrium which leads to pulmonary hypertension and dilation of the heart which are common symptoms of congestive heart failure. A heart then has to work harder pumping blood for the body which can lead to heart damage. Incomplete closing of the mitral valve cusps or leaflets is common, occurring generally in about seven percent of the population. Conditions contributing to incomplete closure of the mitral valve cusps or leaflets include genetic defects, infections, coronary artery disease, myocardial infarction, or congestive heart failure. These conditions contribute to mitral valve regurgitation resulting from enlargement of the mitral valve annulus and/or movement of the papillary muscles away from the valve as a result of ventricular enlargement. When the annulus enlarges, the cusps or leaflets of the valve are no longer able to close (coaptate), because the distance between the two cusps or leaflets has increased too much for the cusps or leaflets to touch each other and thus close off blood flow to the left atrium during, for example, systole. Mitral valve regurgitation can also result as a secondary etiology due to the remodeling of a distorted left ventricle in ischemic heart disease. It is known that as the ventricle is remodeled, the papillary muscles can be displaced away from their natural position. This displacement alters the natural tethering of the cusps or leaflets and restricts the ability of the cusps or leaflets to close properly at the level of the annulus.

In general, most cases of mitral valve regurgitation are mild and the symptoms may be controlled with drugs. In more serious cases, the mitral valve can be repaired through a procedure known as annuloplasty, a surgical procedure in which a synthetic ring is placed around the valve annulus. Annuloplasty encourages aptation of the mitral valve cusps or leaflets by shrinking the size of the valve opening. In other instances, a faulty mitral valve must be surgically replaced with a new valve. These surgical repairs require the opening of the chest by sternotomy or at best through small incisions in the chest wall, heart lung bypass and stopping the heart beat. In general, annuloplasty is an extremely invasive procedure, and, as such, a less invasive treatment for annular dilation is desirable.

SUMMARY

In one embodiment, an apparatus is provided for supporting and/or constricting a surface of a valve annulus. The apparatus includes a tubular member of dimensions suitable for insertion into a body vessel. The tubular member includes at least two first segments attachable to an interior wall of the body vessel. The tubular member further includes at least one second segment which is capable of decreasing its axial length to draw one of the first segments towards the other first segment.

In one embodiment, the tubular member may be used to stabilize or modify a length of a blood vessel. Representatively, when placed, for example, in coronary arteries and/or veins, the tubular member may be used to constrict a surface of an atrioventricular valve annulus, such as the mitral valve annulus that is in close proximity to the coronary arteries and/or veins. The apparatus may also be used to constrict the tricuspid valve annulus. The apparatus and method are useful for treating mitral valve dilation and regurgitation, among other problems. The apparatus may also be used to support and/or constrict other valves or structures in a human or animal body.

In a further embodiment, a method is described. The method includes inserting a tubular member into a body vessel and securing attachable portions of the tubular member to an interior wall of the body vessel. In one implementation, the tubular member secured to the body vessel serves to prevent a portion of the body vessel from increasing in length. In another implementation, the tubular member secured to the body vessel serves to constrict a portion of the body vessel by causing a length of the tubular member between the attachable portions to be reduced.

BRIEF DESCRIPTION OF THE DRAWINGS

The features, aspects, and advantages of the disclosed subject matter will become more fully apparent from the following detailed description and appended claims when taken in conjunction with accompanying illustrations in which:

FIG. 17 is an illustration of an embodiment of a segmented balloon having a first group of segments inflated, and one segment from a second group partially inflated;

FIG. 18 is an illustration of an embodiment of a segmented stent having a first group of segments expanded, and one segment from a second group partially expanded;

FIG. 19 is an illustration of an embodiment of a segmented balloon having a first group of segments inflated, and one segment from a second group fully inflated after being partially inflated;

FIGS. 20 and 21 are illustrations of balloon segments having a range of expandability;

DETAILED DESCRIPTION

In the following description, for purposes of explanation and not limitation, specific details are set forth in order to provide an understanding of the disclosed subject matter. However, it will be apparent to one skilled in the art that the disclosed subject matter may be practiced in other embodiments that depart from these specific details. In some instances, detailed descriptions of well-known methods and devices are omitted so as not to obscure the description of the disclosed subject matter with unnecessary detail.

Figure 1:
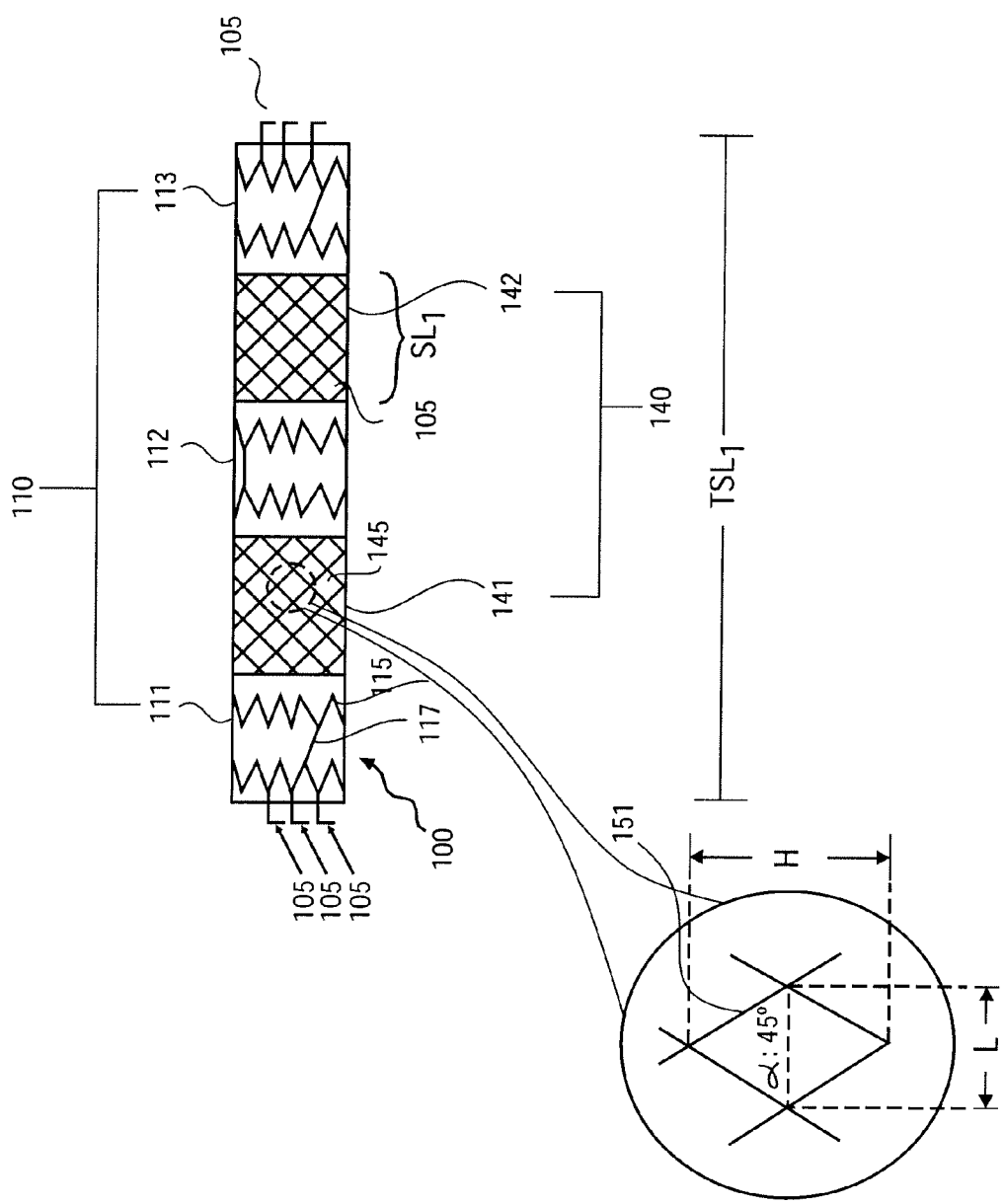
FIG. 1 is an illustration of an embodiment of a segmented stent.

In an embodiment, the apparatus and method relate to stent 100, which is illustrated in FIG. 1. In an embodiment, stent 100 includes a cylindrical body made up of a number of radial fraction segments 110 (e.g., radial traction segments 111, 112 and 113), and one or more shrink segments 140 (e.g., shrink segments 141 and 142). Each radial fraction segment contains a pattern of struts 115. In an embodiment, struts 115 may connect directly to one another, or may be connected by links 117. Struts 115 may be configured in a number of strut patterns, such as multi-link, duet, pentagonal, or others. FIG. 1 shows an embodiment with zig-zag patterned struts 115 and link 117. Stent 100 may be made of a material suitable for residence within a blood vessel. Suitable materials include, but are not limited to, a shaped-memory alloy, nickel titanium, stainless steel alloys, cobalt chrome alloys, nickel alloys and platinum alloys. Stent 100 may include one or more therapeutic or medicinal coatings to improve its compatibility with a blood vessel. Individual segments of stent 100 may also include visualization markers coated thereon or embedded therein (e.g., radiographic, magnetic resonance, etc.).

In one embodiment, stent 100 placed near a mitral valve region may be used to deliver or release a drug or therapeutic agent to treat mitral valve regurgitation. Various drugs are known in the art for treating mitral valve regurgitation. For example, administering nitroprusside (a vascular smooth muscle relaxant) may effectively diminish the amount of mitral regurgitation, thereby increasing forward output by the left ventricle and reducing pulmonary congestion. Inotropic agents such as dobutamine may also be administered to increase the force of contraction of the myocardium. In one embodiment, the stent 100 may be coated with these exemplary drugs for delivery near the mitral valve region. The drugs may have timed-release features to be released slowly over a certain period of time. The drug eluting support annulus or other devices may also have the drug or agent dispersed on the surface of the support annulus or other devices, or co-dissolved in a matrix solution to be dispersed on the support annulus. Methods to coat the support annulus with a therapeutic drug include dip coating, spin coating, spray coating, or other coating methods commonly practiced in the art.

In some cases, patients with defective heart valves may have concomitant coronary artery disease (CAD). As such, it may be advantageous for stent 100 to deliver a drug to treat occlusions in the artery or other related CAD such as vulnerable plaque. The drug to treat CAD may be delivered alone or in combination with drugs to treat mitral valve regurgitation. Drugs to treat CAD include, but are not limited to, statins, lipid lowering agents, antioxidants, extracellular matrix synthesis promoters, inhibitors of plaque inflammation and extracellular degradation, estradiol drug classes and its derivatives.

In one embodiment, the drugs to treat CAD may be coated on a stent 100 using methods such as dip coating, spin coating, spray coating or other coating methods known in the art. The drug may alternatively be encapsulated in microparticles or nanoparticles and dispersed in a coating on the support annulus or other device. A diffusion limiting top-coat may optionally be applied to the above coatings. The active agents may optionally be loaded on a support annulus or other device together either by adding them together to the solution of the matrix polymer before coating, or by coating different layers, each containing a different agent or combination of agents. The drug eluting the stent may alternatively have an active agent or a combination of agents dispersed in a bioerodable annulus forming polymer.

Stent 100 is of dimensions suitable to be inserted into a body lumen, such as the coronary arteries or coronary veins. In one implementation, the stent 100 is of dimensions suitable to be inserted into a right coronary artery or the circumflex branch. After insertion, each radial traction segment 110 may be expanded by a balloon or other known method. Upon expansion, struts 115 may make radial contact with the inner surfaces of the body lumen so as to maintain stent 100 in a fixed position in the body lumen.

Figure 28A:
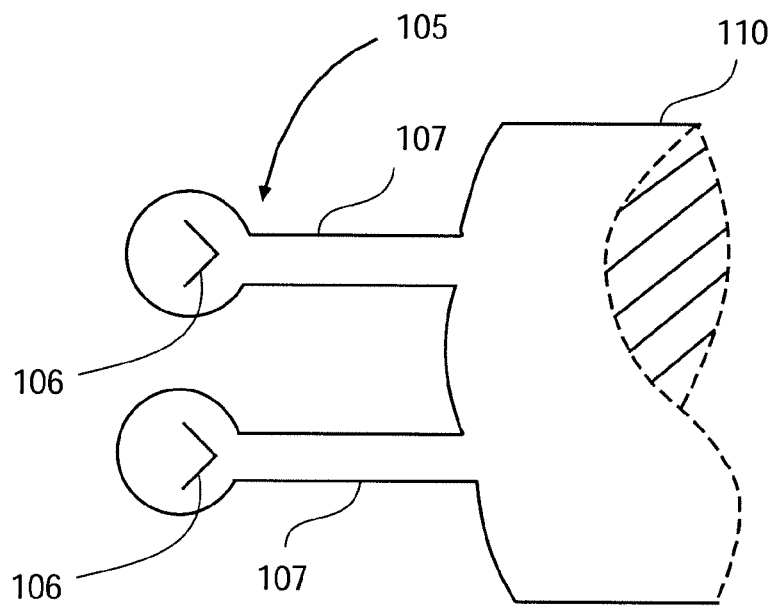
FIGS. 28A-28C are illustrations of various embodiments of a hooks connected to a traction segment.
Figure 28B:
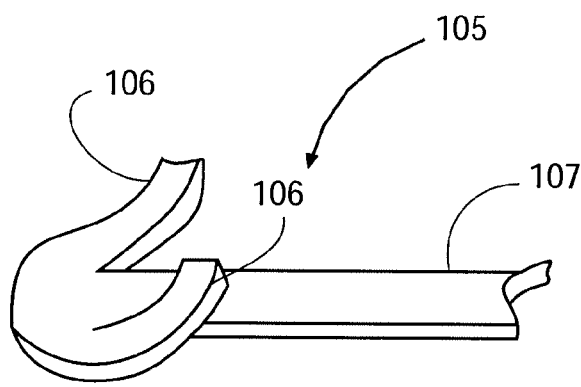
Figure 28C:
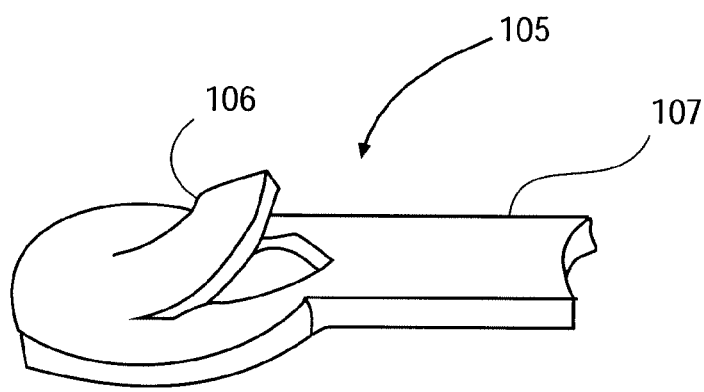

In an embodiment, stent 100 may also include hooks 105, which may be coupled to radial fraction segments 110. The hooks 105 may be embodied in various shapes and forms. FIGS. 28A-28C represent various hook members 105 that may be used with the stent 100. In the illustrated embodiments, the hook members 105 include one or more sharp sections 106 provided at one end thereof. The sharp sections 106 formed on the hook members permit the stent to firmly attach to an interior wall of a body vessel, as the radial traction segments are radially expanded. As shown in FIG. 28A, the hook member 105 may also include an arm section 107 extending between traction segment 110 and the sharp sections 106.

In an embodiment, hooks 105 are only connected to radial fraction segments 110 located at either horizontal ends of stent 100 (e.g., radial traction segment 111 and 113, respectively, in the embodiment shown in FIG. 1). In other embodiments, hooks 105 may also be coupled to radial traction segments 110 that lie in the interior of stent 100. Upon expansion of radial fraction segments 110, hooks 105 will be seated in an inner surface(s) of the body lumen to provide further radial fraction. It is appreciated that hooks 105 may also be coupled to segments 140 in other embodiments, or may be attached to any structures placed at either horizontal end of stent 100 or any structures placed between radial traction segments 110 and/or 140.

As stated above, in an embodiment, stent 100 also includes one or more shrink segments 140 (e.g., linear shrink segments). Shrink segments 140 may include struts 145. Struts 145 are biased at angles so that as shrink segment 140 is expanded, shrink segment 140 decreases in longitudinal length. When one or more shrink segments decrease in length, the overall length of stent 100 decreases, thus constituting an inner surface of the body lumen in which stent 100 is seated.

Figure 27A:
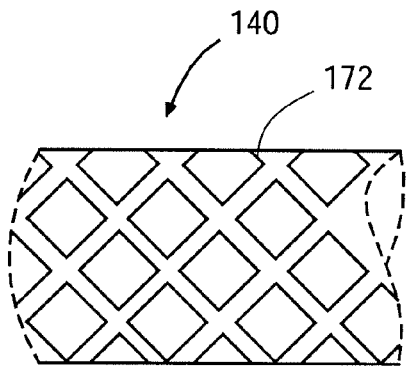
FIGS. 27A-27D are illustrations of various embodiments of a shrink segment.
Figure 27B:
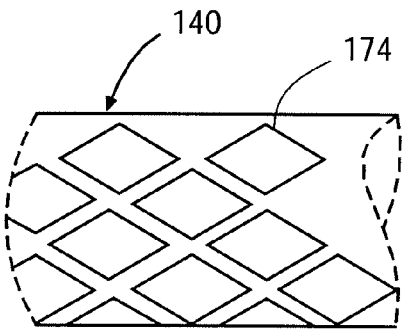
Figure 27C:
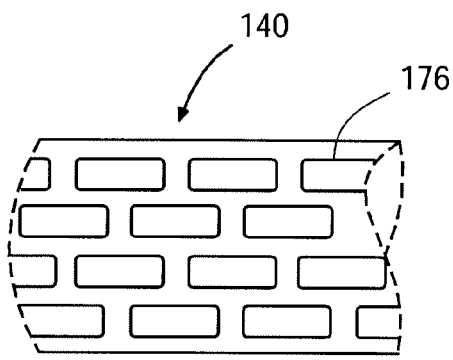
Figure 27D:
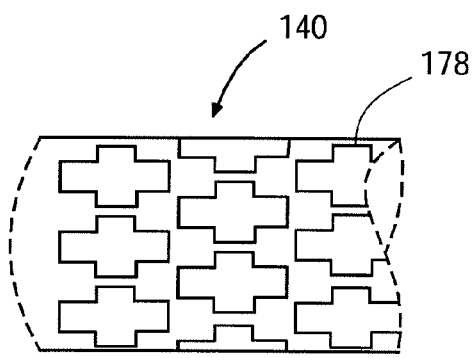

Various patterns may be used to construct a shrink segment. FIGS. 27A-27D represent a number of patterns that may be used in shrink segments 140. The shrinks segments shown in FIGS. 27A-27D include a number of radially expandable cells. In one embodiment, each radially expandable cell is configured such that, as the cell is expanded in a radial direction, its axial length will decrease. FIG. 27A is an illustration of an embodiment of the shrink segment 140, in which each radially expandable cell 172 has a square configuration with struts disposed in slanted orientation with respect to a longitudinal axis of the shrink segment. FIG. 27B is an illustration of an embodiment of the shrink segment 140, in which each radially expandable cell 174 has a diamond configuration. FIG. 27C is an illustration of an embodiment of the shrink segment 140 having an alternating slots pattern 176. It is to be appreciated that the slot pattern 176 formed in the shrink segment shown in FIG. 27C will deform as the shrink segment is radially expanded, causing its longitudinal length to decrease. FIG. 27D is an illustration of an embodiment of the shrink segment 140 having an alternating axial/radial slots pattern 178.

Figure 3:
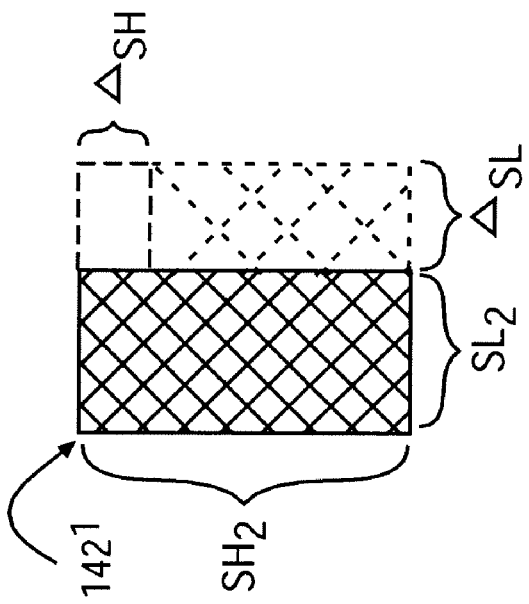
FIG. 3 is a close up illustration of expanded shrink segment.
Figure 2:
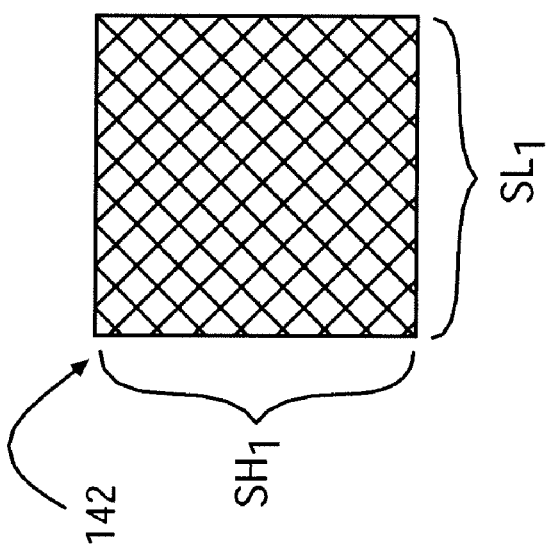
FIG. 2 is a close up illustration of an embodiment of unexpanded shrink segment.

FIG. 2 is a close up illustration of an embodiment of unexpanded shrink segment 142. FIG. 3 is a close up illustration of shrink segment 142 following expansion (designated expanded shrink segment 142'). Shrink segment 142 may be expanded in a radial direction by various means, including with a balloon. In an unexpanded state, shrink segment 142 has a longitudinal length of $SL_1$ and a radial height $SH_1$. Following expansion from $SH_1$ to $SH_2$ (FIG. 3), shrink segment 142' has a longitudinal length $SL_2$, which is less than $SL_1$. Accordingly, when hooks 105 have been seated, and shrink segments 140, including shrink segment 141 and shrink segment 142, are expanded, the length of shrink segments 140 will each decrease from $SL_1$ to $SL_2$. The reduction in the length of segments 140 will cause radial traction segments 110 to be pulled toward one another, thereby reducing an overall length of stent 100. Referring again to FIG. 2 and FIG. 3, when the radial height of shrink segment 142 is increased by $\Delta_{SH}$ (i.e., $SH_2$ to $SH_1$), the longitudinal length of shrink segment 142 is decreased by $\Delta_{SL}$ (i.e., $SL_1$ to $SL_2$). In embodiments, the ratio of $\Delta_{SL}:\Delta_{SH}$ may be varied by modifying the pattern of struts 115. As described below, struts 115 may be designed such that the $\Delta_{SL}:\Delta_{SH}$ ratio is 2:1, 1:1, 1:2 or other ratios.

Referring again to FIG. 1, in an unexpanded state, stent 100 has a total length defined as $TSL_1$. Stent 100 can be manufactured with a length that is suitable for insertion into a coronary sinus or circumflex branch of the left coronary artery. The coronary sinus and circumflex branch are positioned, in a typical heart, exterior to the left atrium and left ventricle approximate portions of the mitral valve annulus. Stent 100 can be placed in one or both of the coronary sinus and circumflex branch to inhibit the mitral valve annulus from lengthening (e.g., getting larger in diameter). By constricting a portion of the coronary sinus and/or circumflex branch in this area, an atrioventricular valve annulus (e.g., mitral valve annulus) can also be constricted to an appropriate degree. Representatively, in terms of the mitral valve, by constricting the mitral valve annulus, cusps or leaflets can be brought closer together to improve aptation (coaptation) and reduce regurgitation. Additionally, the height and length of the various segments 110 and 140 may vary so as to construct stent 100 in a shape that is tapered to conform with the particular blood vessel or body lumen into which it is inserted.

Stent 100 may include various combinations of radial traction segments 110 (segment 111, segment 112, and segment 113) and shrink segments 140 (segment 141 and segment 142). For example, in the embodiment illustrated in FIG. 1, stent 100 includes alternating radial traction segments 110 with one shrink segment 140 disposed between each of radial traction segments 110. In other embodiments, stent 100 could include a number of radial traction segments 110 placed adjacent to one another, or a number of shrink segments 140 placed adjacent to one another. It is also appreciated that stent 100 may include various quantities of shrink segments 140. The embodiment of stent 100 illustrated in FIG. 1 includes three radial fraction segments 110 and two shrink segments 140. However, in other embodiments, stent 100 may include only one shrink segment 140, or more than two shrink segments 140. Stent 100 may include any number of radial traction segments 110. Additionally, the quantity of radial traction segments 110 may be even or odd, and the quantity of shrink segments 140 may also be even or odd.

Figure 4:
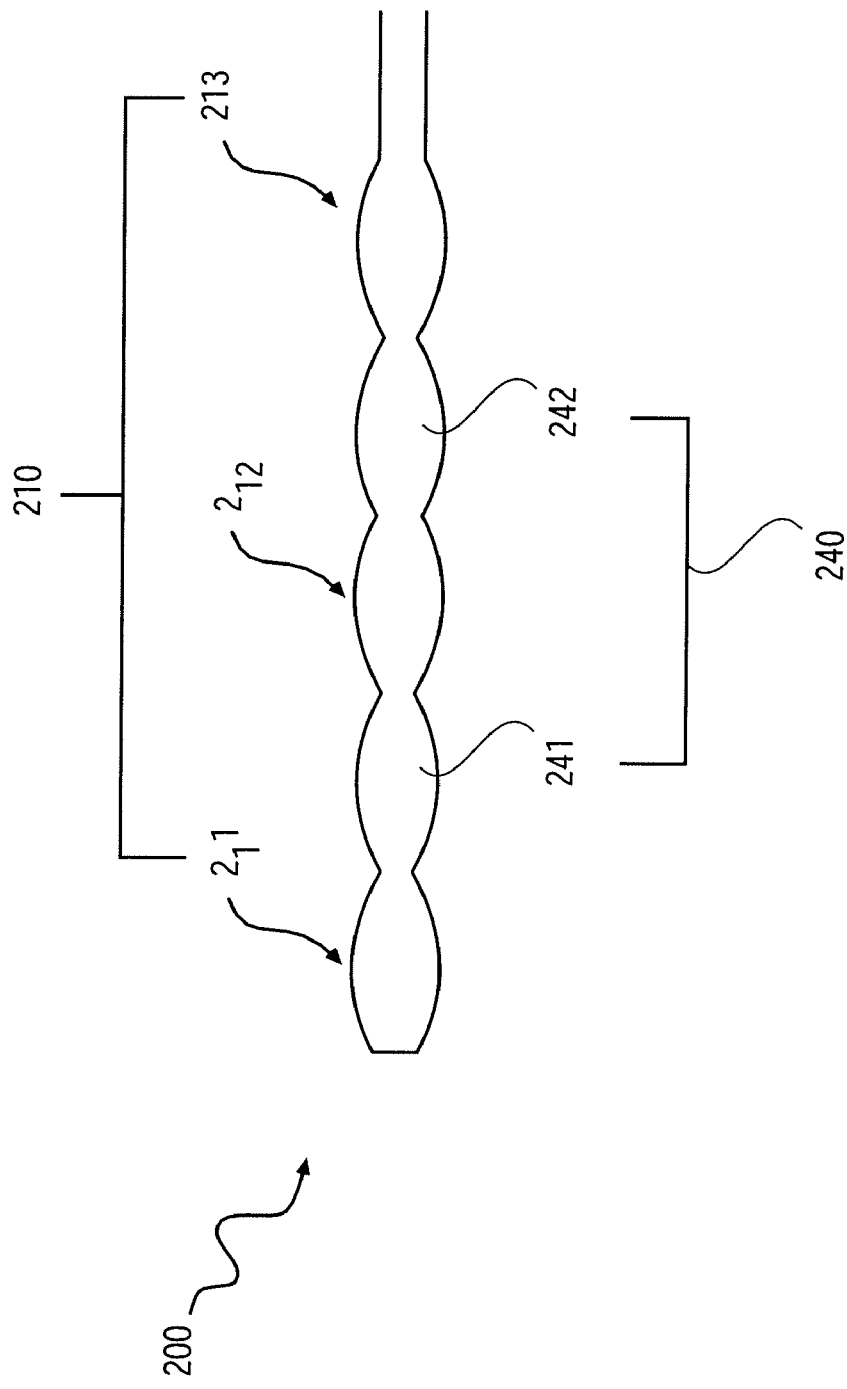
FIG. 4 is an illustration of an embodiment of a segmented balloon.

FIG. 4 is an illustration of an embodiment of segmented balloon 200. In an embodiment, balloon 200 includes a number of segments that correspond to segments of stent 100 (FIG. 1). Representatively, in FIG. 2, balloon segments 211, 212 and 213 correspond to radial traction stent segments 111, 112 and 113 of stent 100. Balloon segment 241 corresponds to shrink stent segment 141 and balloon segment 242 corresponds to shrink stent segment 142 of stent 100. Balloon segments 211, 212, 213, 241 and 242 may be inflated individually, in groups, or all at once. Additionally, balloon segments 211, 212, 213, 241 and 242 may be either partially inflated to varying degrees or may be completely inflated. If balloon segments 211, 212, 213, 241 and 242 are fully inflated, the corresponding stent segments will be expanded to a first degree. In an embodiment, if balloon segments 211, 212, 213, 241 and 242 are partially inflated, they will exert a force on the corresponding stent segments that will cause the corresponding stent segments to expand to a degree that is less than the first degree.

Figure 5:
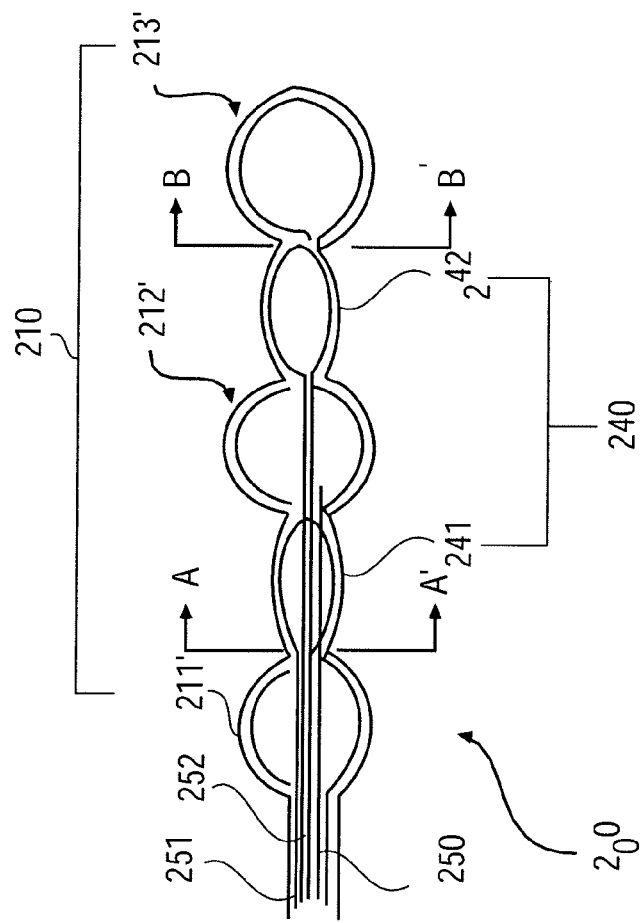
FIG. 5 is an illustration of an embodiment of a segmented balloon having segments inflated to correspond with a first group of segments of a stent.

FIG. 5 is an illustration of an embodiment of segmented balloon 200 in which only a group of balloon segments corresponding to radial fraction segments 110 have been inflated. A suitable balloon material is similar to dilation catheter balloons or stent placing balloons. Balloons 200 may be inflated according to conventional techniques, for example, suitable liquid delivered at a proximal end of a catheter. Segments 211, 212 and 213, which correspond to radial traction segments 110 of stent 100, may be expanded individually, all at once, or in groups. Upon expansion, balloon segments 211, 212 and 213 will exert force on the respective corresponding stent segments (i.e., stent segments 111, 112 and 113), therefore causing these stent segments to expand. The embodiment of segmented balloon 200 illustrated in FIG. 5 includes five inflatable segments corresponding to radial traction segments and shrink segments of the stent 100. However, in other embodiments, segmented balloon may include any number of inflatable segments (e.g., 1, 2, 3, 4, etc). For example, the same inflatable segment of the balloon may be used to expand more than one segment of the stent by deflating the inflated segment, realigning the inflatable segment to align with another segment of the stent and reinflating the balloon segment.

Figure 5A:
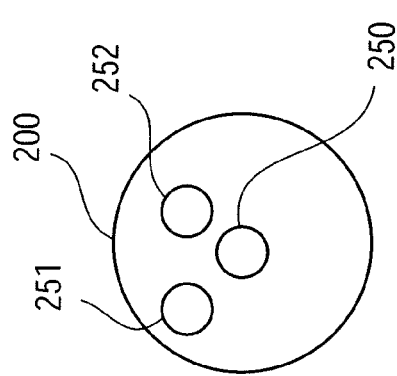
FIG. 5A is an illustration of a cross-sectional view of the segmented balloon taken along line A-A' of FIG. 5.
Figure 5B:
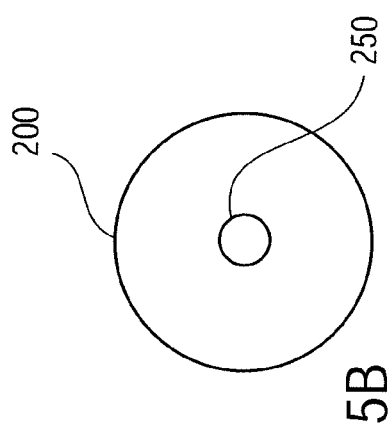
FIG. 5B is an illustration of a cross-sectional view of the segmented balloon taken along line B-B' of FIG. 5.

In one embodiment, the segmented balloon 200 includes a number of lumens with separate lumens for inflating separate balloon segments (e.g., by delivering liquid to separate segments of the balloon). For example, as seen by referring to FIG. 5A, a cross-sectional view of the segmented balloon taken along line A-A' of FIG. 5 shows multiple-lumens. In the embodiment illustrated in FIG. 5A, there are three lumens 250-252. One lumen 250 is provided in the segmented balloon to inflated all segments 211, 212 and 213, which correspond to radial traction segments 110 of stent 100. The other lumens 251 and 252 are provided to inflate individual segments 241 and 242, which correspond to shrink segments 140 of stent 100. By providing individual lumens 251 and 252 for the segments 241 and 242, one segment of the segmented balloon 200 may be inflated independent of other segments of the balloon 200. FIG. 5B shows cross-sectional view of a distal end of the segmented balloon taken along line B-B' of FIG. 5. As shown in FIG. 5B, only one lumen 250 corresponding to the last remaining segment 213 is provided at the distal end of the segmented balloon. In the illustrated embodiment, three lumens 250-252 are shown; however any number of lumens may be provided in a segmented balloon to allow one or more segments to be inflated independent of other inflatable segments.

Figure 6:
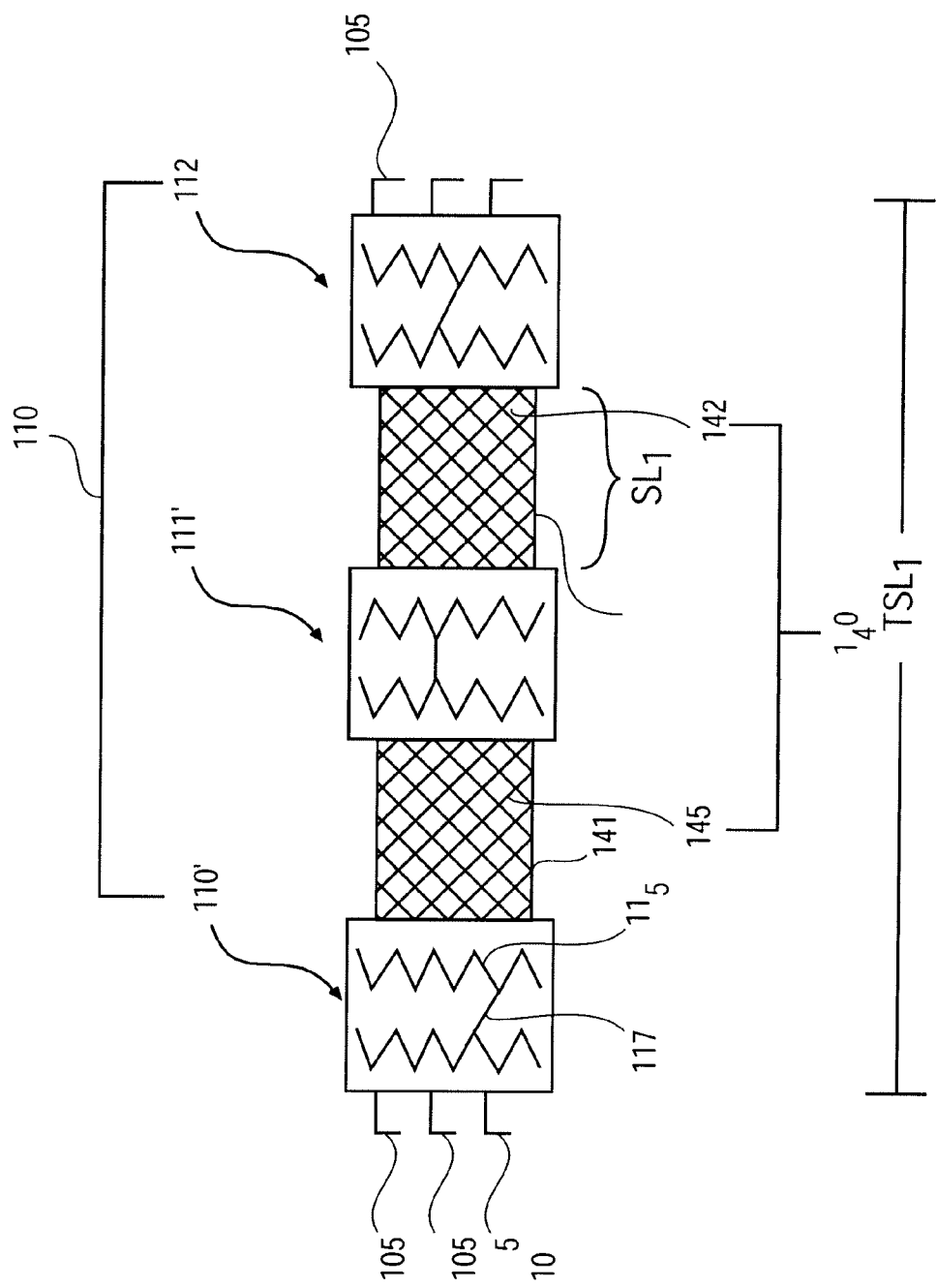
FIG. 6 is an illustration of an embodiment of a segmented stent having a first group of segments expanded and a second group of unexpanded segments.

FIG. 6 is an illustration of an embodiment of stent 100 after balloon 200 has been inflated in the manner illustrated in FIG. 5. As shown in FIG. 6, upon inflation of balloon 200 in this manner, segments 111, 112 and 113 of stent 100 will be expanded, but segments 141 and 142 of stent 100 will not be significantly expanded. In an embodiment, the expansion of stent segments 110 will seat hooks 105 into an inner surface of a body lumen such as the interior wall of the coronary sinus surrounding the mitral valve annulus to provide radial traction between stent 100 and an inner surface of a body lumen.

Figure 7:
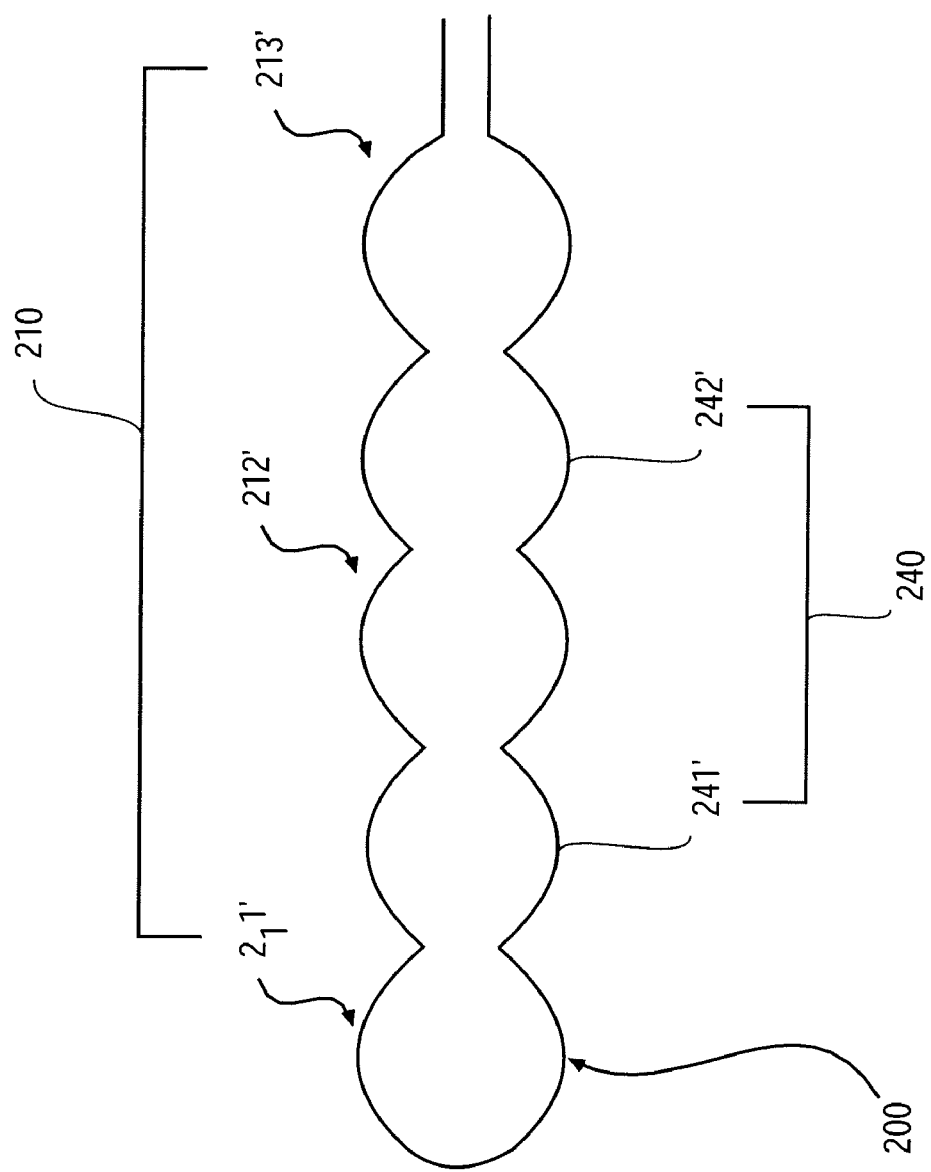
FIG. 7 is an illustration of an embodiment of a segmented balloon having segments inflated to correspond with a first group and a second group of segments of a stent.
Figure 8:
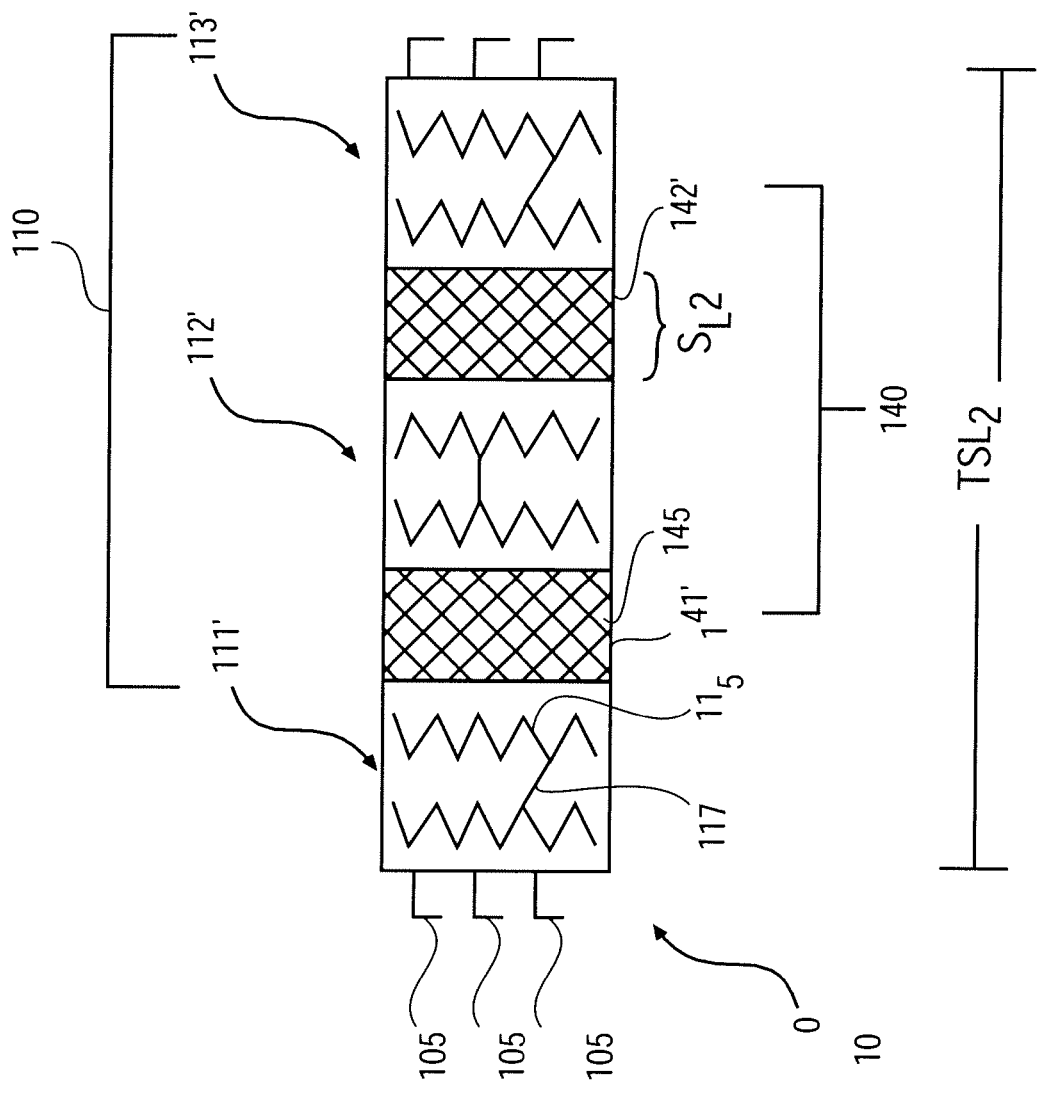
FIG. 8 is an illustration of an embodiment of a segmented stent having segments of a first group and segments of a second group expanded.

FIG. 7 is an illustration of an embodiment of segmented balloon 200 having balloon segments 241 and 242, which correspond to linear shrink segments 141 and 142, respectively, inflated, in addition to segments 211, 212 and 213 (See FIG. 3). As balloon segments 241 and 242 are inflated, force is applied to linear shrink segments 141 and 142, thus causing expansion of segments 141 and 142. FIG. 8 is an illustration of an embodiment of stent 100 after expansion of linear shrink segments 141 and 142. As discussed above, the longitudinal length of linear shrink segments 140 reduces from a length $SL_1$ (prior to expansion) to a length of $SL_2$ upon expansion. As such, upon expansion, the total length of stent 100 is reduced by a length of $R \times (SL_1 - SL_2)$, where R is the total number of segments 140 that are expanded. The total length of stent 100 following expansion of segments 140 is defined as $TSL_2$.

In one embodiment, the linear shrink segments 141 and 142 are radially expanded one at a time. For example, after one segment of the balloon has been inflated to radially expand one of the linear shrink segments 141 and 142, the inflated segment of the balloon may be deflated prior to adjustment of a different shrink segment. It should be noted that once the catheter balloon has been used to reduce a length of one of the linear shrink segments, realignment of the balloon with respect to the stent (e.g., by using visualization markers such as radiopaque markers) may be necessary prior to adjustment of different shrink segment.

In another embodiment, two or more linear shrink segments (e.g., segments 141 and 142) may be radially expanded at the same time. In this embodiment, the segmented balloon may be configured so that, as each linear shrink segment reduces in its longitudinal length, the individual inflatable segments of the balloon will maintain proper alignment with the individual segments of the stent.

Referring to FIGS. 1 and 27A-27D, a shrink segment may includes a number of radially expandable cells, in which each cell is configured such that, as the cell is expanded in a radial direction, its axial length will decrease. In embodiments shown in FIGS. 1, 27A and 27B, each radially expandable cell is formed with a number of slated struts configured such that, as each cell is expanded in a radial direction, a bias angle between the slated struts and a longitudinal axis increases to cause its axial length to decrease. It is to be appreciated that, the angles between struts 145 in linear shrink segments 140 may be biased at different angle so as to control the degree of reduction in length of each linear shrink segment 140 upon expansion.

Representatively, FIG. 1 illustrates an embodiment in which the struts of each unit cell 151 are biased at 45° angles (angled α). As each unit cell 151 is expanded in the radial direction, the bias angle between the diagonally disposed elements and the longitudinal axis will increase, causing the longitudinal length (L) of each unit cell 151 to decrease. Upon expansion, at a 45° strut bias, the longitudinal length shrinkage:vertical height expansion ratio for each unit cell 151 is 1:1. Specifically, upon expansion, the reduction in longitudinal length (L) of the individual unit cell 151 is substantially equal to the increase in vertical height (H) of the cell 151. It should be understood that the amount of linear shrinkage of a shrink segment is function of the number of unit cells around the circumference of the shrink segment and the number of unit cells in the longitudinal direction.

In one embodiment, a shrink segment is capable of shrinking greater than 10% in the longitudinal direction. In another embodiment, a shrink segment is capable of shrinking greater than 25% in the longitudinal direction. For example, in one implementation, for a shrink segment having struts biased at 45° angles, a longitudinal length of 6.8 mm and a diameter of 2 mm, an increase in the diameter of 0.5 mm will cause a 2.66 mm reduction in the longitudinal length.

Figure 9:
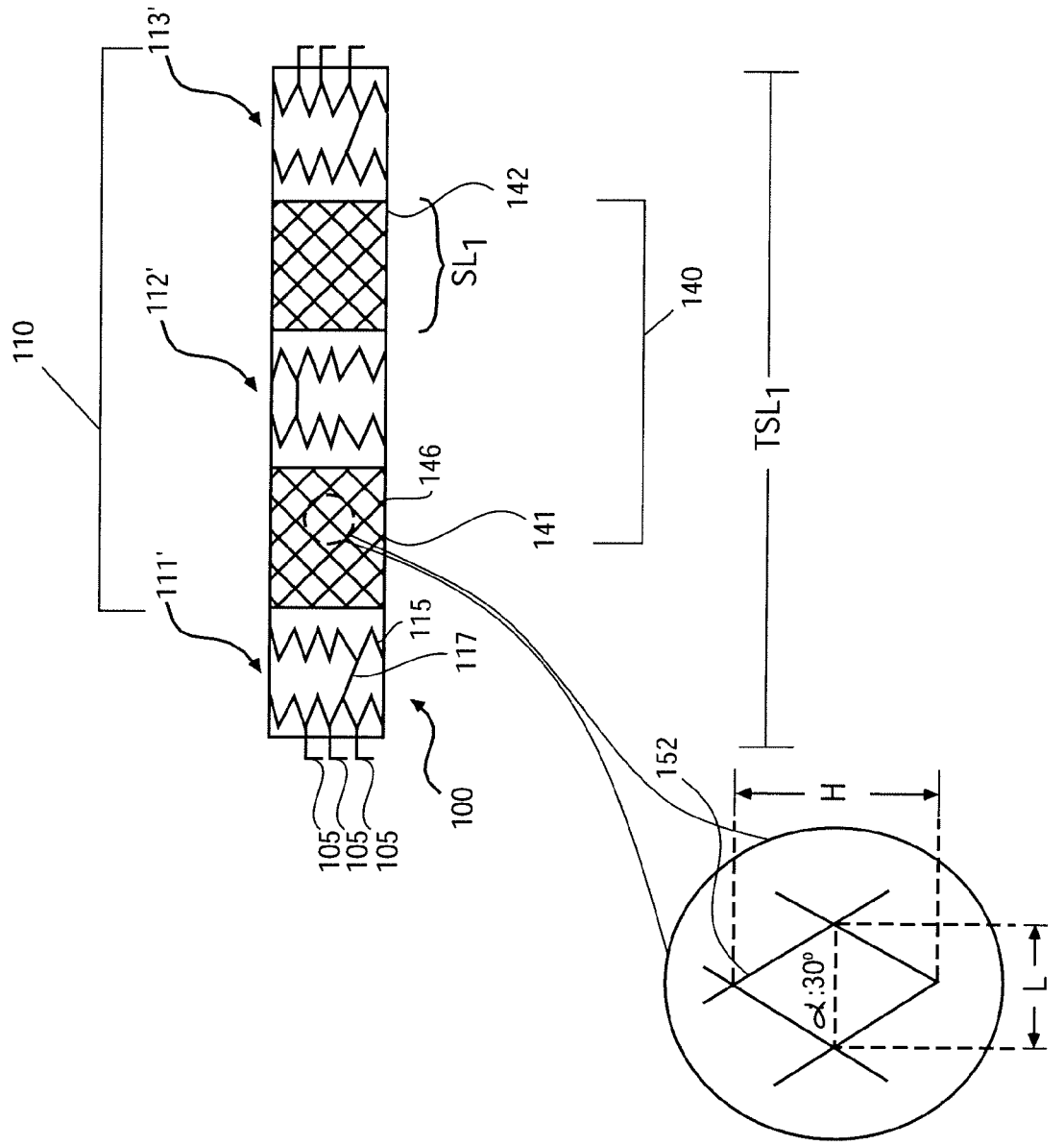
FIG. 9 is an illustration of an embodiment of a segmented stent having a group of segments with struts angled at a 30-degree angle.
Figure 10:
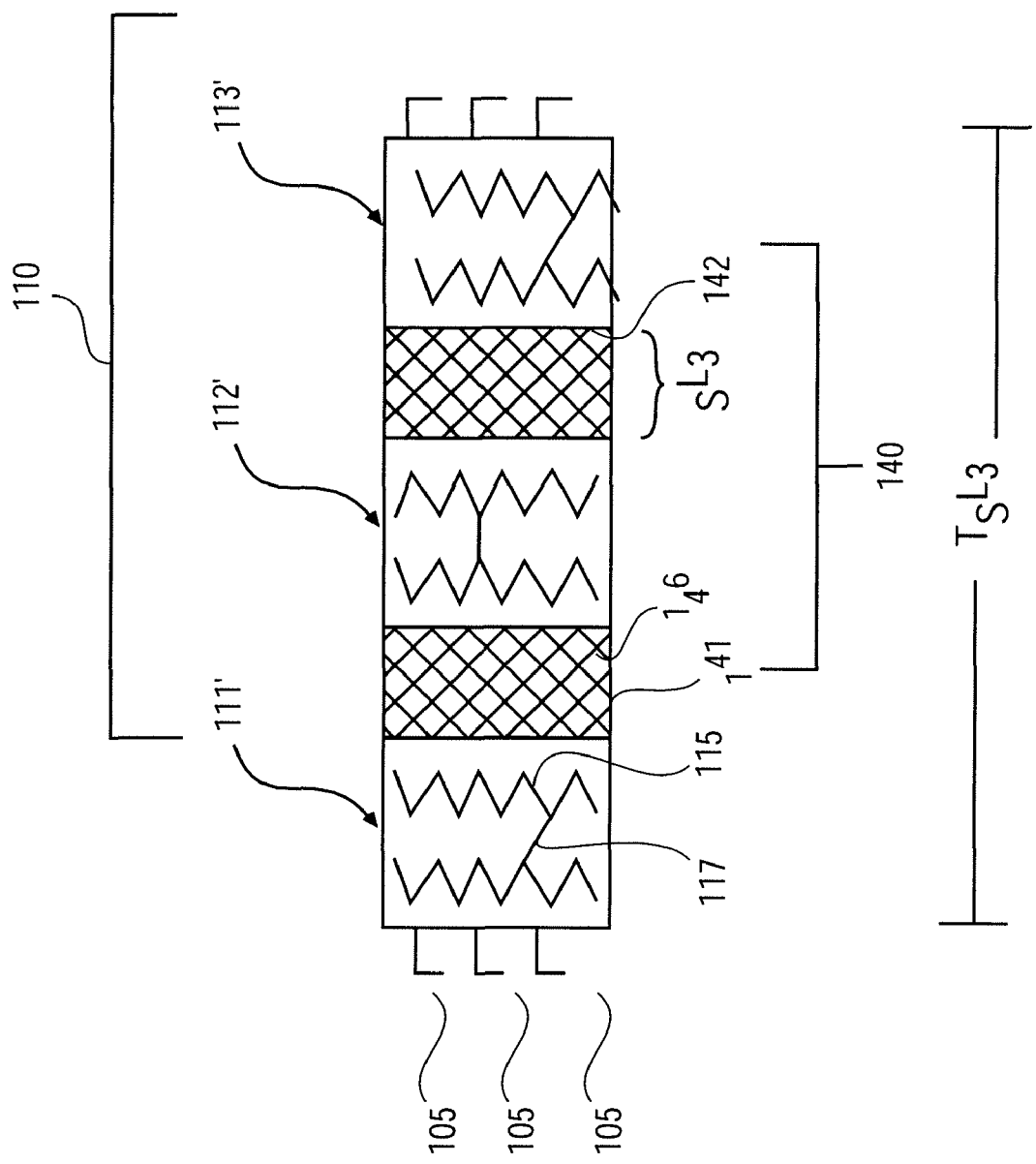
FIG. 10 is an illustration of an embodiment of a segmented stent having a first group of segments with struts angled at a 30 degree angle, wherein the segments are expanded.

In another embodiment, illustrated by FIG. 9, struts 145 are biased at a 30° angle (angled a). Upon expansion, at a 30° strut bias, the longitudinal length shrinkage:vertical height expansion ratio for each unit cell 152 is 2:1. As such, upon expansion, the reduction in longitudinal length (L) of the individual cell 152 may be approximately twice the increase in vertical height (H) of the cell 152. Accordingly, when a 30° strut bias is employed, the total length of stent 100 will be reduced to length $TSL_3$ that is shorter than the total length $TSL_2$ of stent 100 when it is shrunk with struts 140 at a 45° strut bias. The bias angle is measured relative to a longitudinal axis of the stent. It is appreciated that struts 145 may be biased at various different angles as one means of regulating the degree of longitudinal shrinkage of stent 100.

Figure 11:
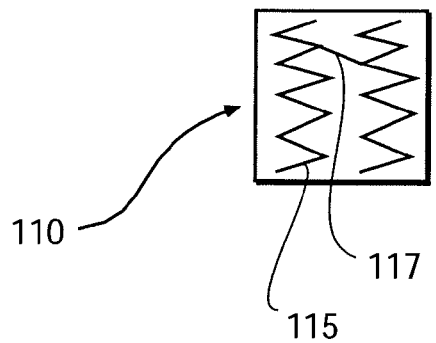
FIGS. 11-14 are illustrations of various embodiments of a radial traction segment.
Figure 12:
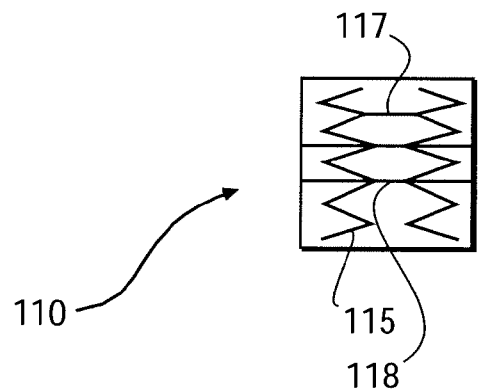
Figure 13:
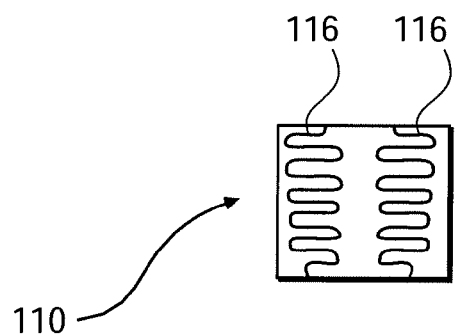
Figure 14:
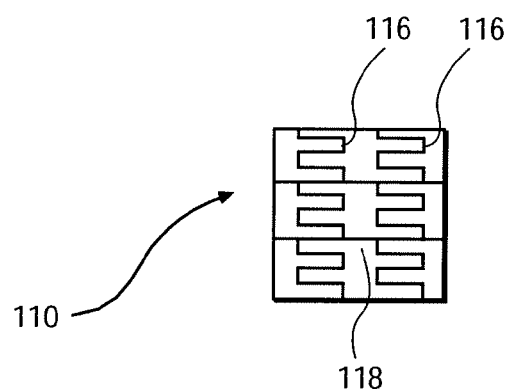

As discussed above, in regard to radial fraction segments 110, various strut designs are adequate and can be used to practice the disclosed subject matter. In one embodiment, the traction segments 110 are configured to maintain its axial length substantially constant as the traction segments 110 are expanded in a radial direction. FIGS. 11-14 represent a number of strut designs that may be used in radial traction segments 110. FIG. 11 is an illustration of an embodiment of radial traction segment having struts 115 in a zig-zag pattern. In an embodiment, a radial traction segment 100 also includes link 117. One or more struts may be connected by link 117. FIG. 12 is an illustration of an embodiment of radial traction segment 110 having struts in a zig-zag pattern, and having an additional cross strut. The cross struts tend to add to the tensile strength of the segment. FIG. 13 is an illustration of an embodiment of radial fraction segment 110 having a loop pattern of struts. FIG. 14 is an illustration of an embodiment of a stent segment having a loop pattern with an additional cross strut. The cross struts tend to add to the tensile strength of the segment.

Figure 15:
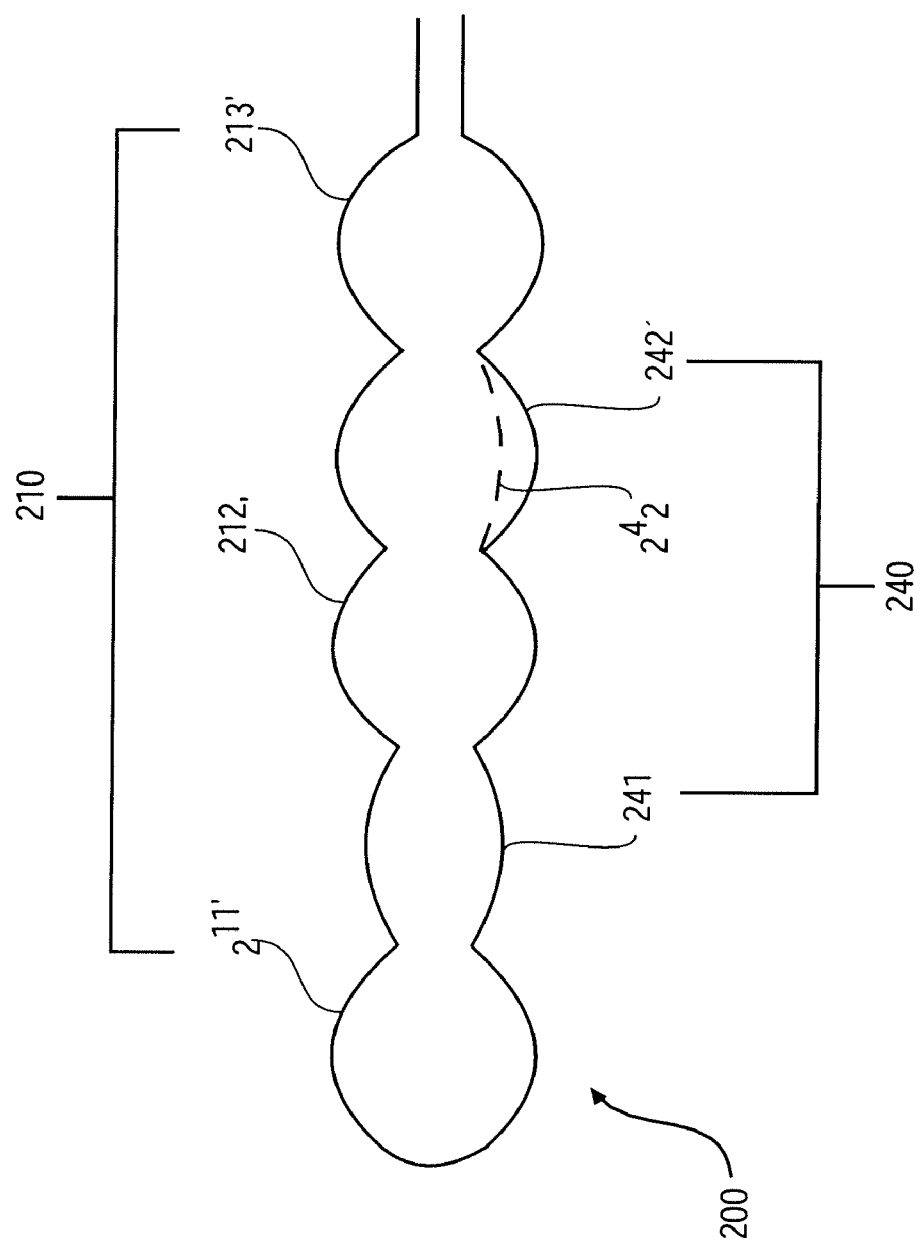
FIG. 15 is an illustration of an embodiment of a segmented balloon having a first group of segments inflated, and one segment from a second group inflated.
Figure 16:
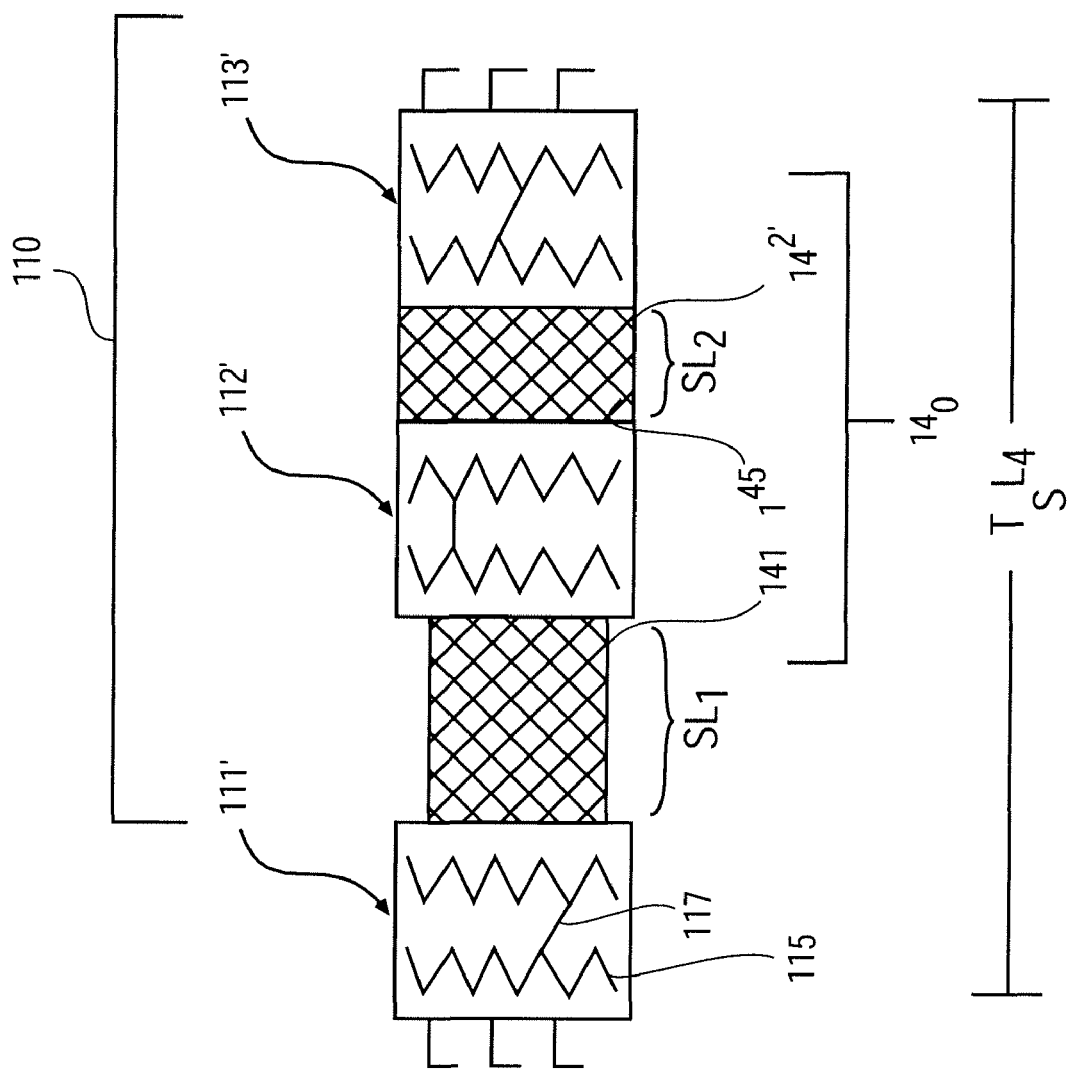
FIG. 16 is an illustration of an embodiment of a segmented stent having a first group of segments expanded, and one segment from a second group expanded.

In an embodiment, stent 100 and balloon 200 may be configured to expand each linear segment 140 of stent 100 individually, in groups, or all at once. One way this may be accomplished is through a multi-lumen balloon 200 (e.g., with separate lumens corresponding to separate balloon segments). As stated above, in an embodiment, segments 211, 212 and 213 corresponding to radial fraction segments 110 (e.g., radial fraction segments 111, 112 and 113, respectively) are typically first inflated to seat hooks 105. After hooks 105 have been seated, in an embodiment, linear shrink segments 141 and 142 may be expanded one at a time by expanding individual balloons corresponding to each particular segment. In this regard, FIG. 15 is an illustration of an embodiment of balloon 200 in which, among the balloon segments corresponding to linear shrink segments, only segment 242 corresponding to a shrink segment 142 is inflated (inflation illustrated by reference numeral 242'). Segment 241 is not inflated and, as such, shrink segment 141 that corresponds to balloon segment 241 will not expand. FIG. 16 is an illustration of stent 100 following inflation of balloon 200 as illustrated in FIG. 15. Upon expansion of stent segment 142, the total length of stent 100 will be reduced from length $TSL_1$ to length $TSL_4$. In an embodiment, length $TSL_4$ will be greater than length $TSL_2$, which as described above, was obtained when all shrink segments 140 were expanded at the same time, as illustrated in FIG. 8. As such, by inflating balloon segments 240 one at a time, or in a group that does not include all balloon segments 240, the degree of reduction in length of stent 100 will be reduced. Additionally, in an embodiment, by inflating balloon segments 210 one at a time, or in groups, stent 100 may be gradually reduced to size $TSL_1$, which is a length of stent 100 after all linear shrink segments 140 have been expanded. Balloon segments 240 may be expanded over varying periods of time, as required by the person administering stent 100. For example, one linear shrink segment 140 could be expanded to introduce a first degree of reduction in the length of stent 100. Then, a few months later (or whatever time frame is determined to be appropriate), another balloon segment 240 may be inflated to expand a different linear shrink 140, thereby further reducing the total length of stent 100.

In an embodiment, balloon segments 240 may be partially inflated so as to partially expand stent segments 140. FIGS. 17-18 are embodiments of balloon segment 242 partially inflated to a height $H_1$ (illustrated by reference numeral 242'). By partially expanding stent segments 140, the degree of reduction in the length of linear shrink segments 140 will be less than the degree of reduction in length that is obtained when shrink segments 140 are completely expanded. In this regard, FIG. 19 illustrates stent 100 following inflation of balloon 200 in the manner illustrated in FIGS. 17-18. Shrink segment 142 is partially expanded to reduce the length of shrink segment 142 to length $SL_I$. $SL_I$ is greater than $SL_2$, which is the length of shrink segment 142 upon full expansion. As a result of this reduction in the length of linear shrink stent segment 142, the total length of stent 110 is reduced to $TSL_5$, which is greater than the length of stent 110 if linear shrink stent segment 142 is fully expanded.

Figure 22:
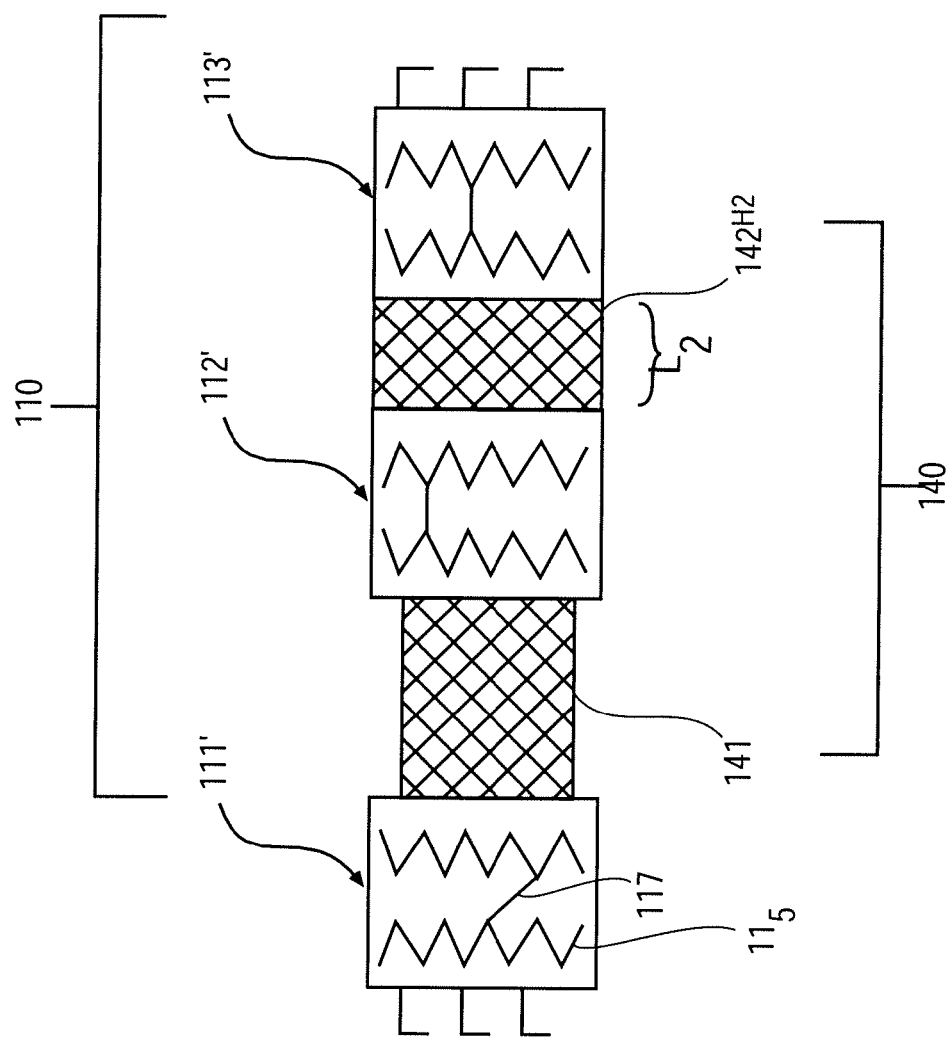
FIG. 22 is an illustration of an embodiment of a segmented stent having a first group of segments expanded, and one segment from a second group fully expanded after being partially expanded.

As shown in FIGS. 20-21, in an embodiment, balloon segments 240 may be further inflated so as to further expand partially expanded shrink segments 140. For example, balloon segment 242, which, as shown in FIGS. 17-18, may be expanded to intermediate height $H_1$, may be further expanded to $H_2$. Upon this further expansion of segment 242, the corresponding linear shrink segment will be further expanded and shrink longitudinally as shown in FIG. 22 (illustrated by reference numeral 242"). In this manner, the length of stent 110 may be gradually reduced. In such embodiments, balloon segments 140 may be partially inflated, and then further inflated any number of times so as to gradually reduce the length of a shrink segment 140, and to gradually reduce the overall length of stent 110. In an embodiment, balloon segments 240 may be further inflated until full expansion, thereby fully expanding corresponding stent segments 110.

Figure 23:
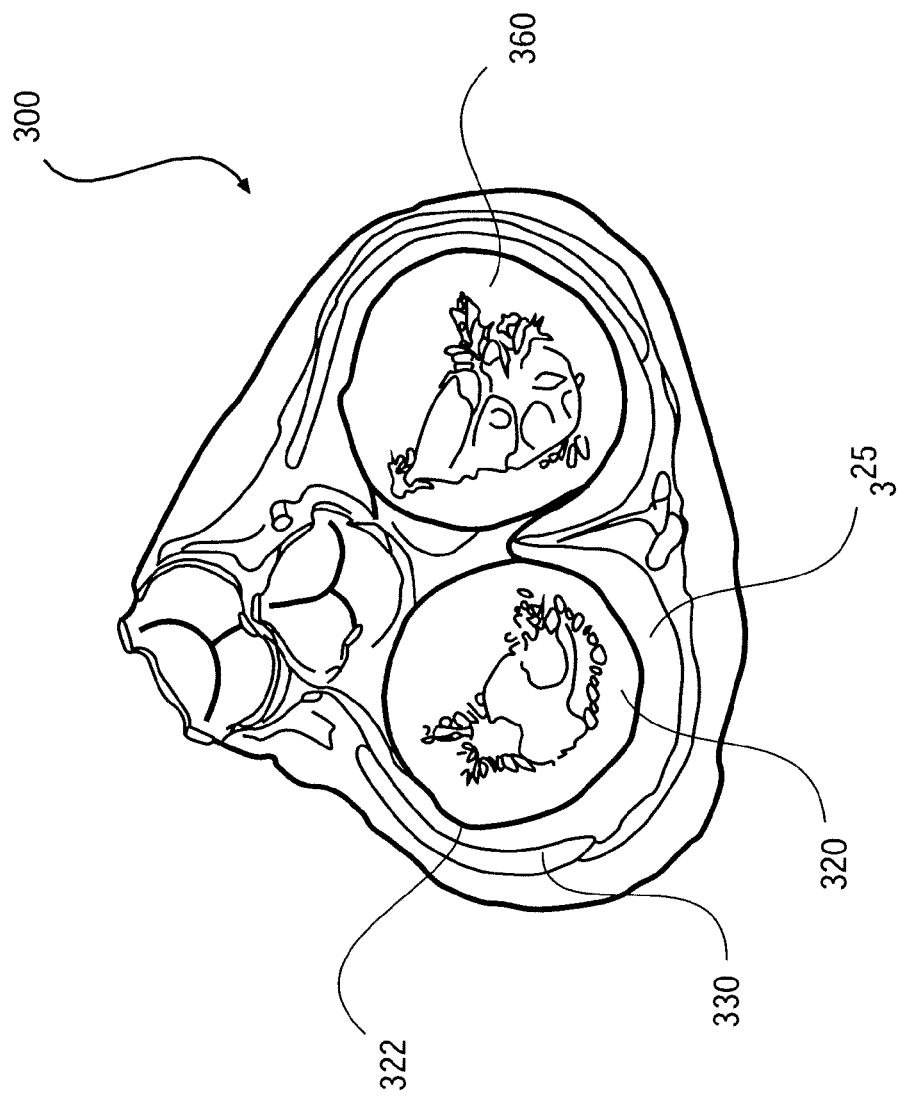
FIG. 23 is an illustration of an embodiment of a human heart.

FIG. 23 is a diagram showing a top cross-section of human heart 300 taken through the right and left atrium. Human heart 300 includes mitral valve 320 and tricuspid valve 360. Mitral valve 320 is substantially surrounded by mitral annulus 325. A portion of circumflex branch 330 runs close (externally adjacent) to a portion of mitral valve 320, exterior to the left atrium and left ventricle. A portion of coronary sinus also extends close (externally adjacent) to a portion of mitral valve 320.

Figure 24:
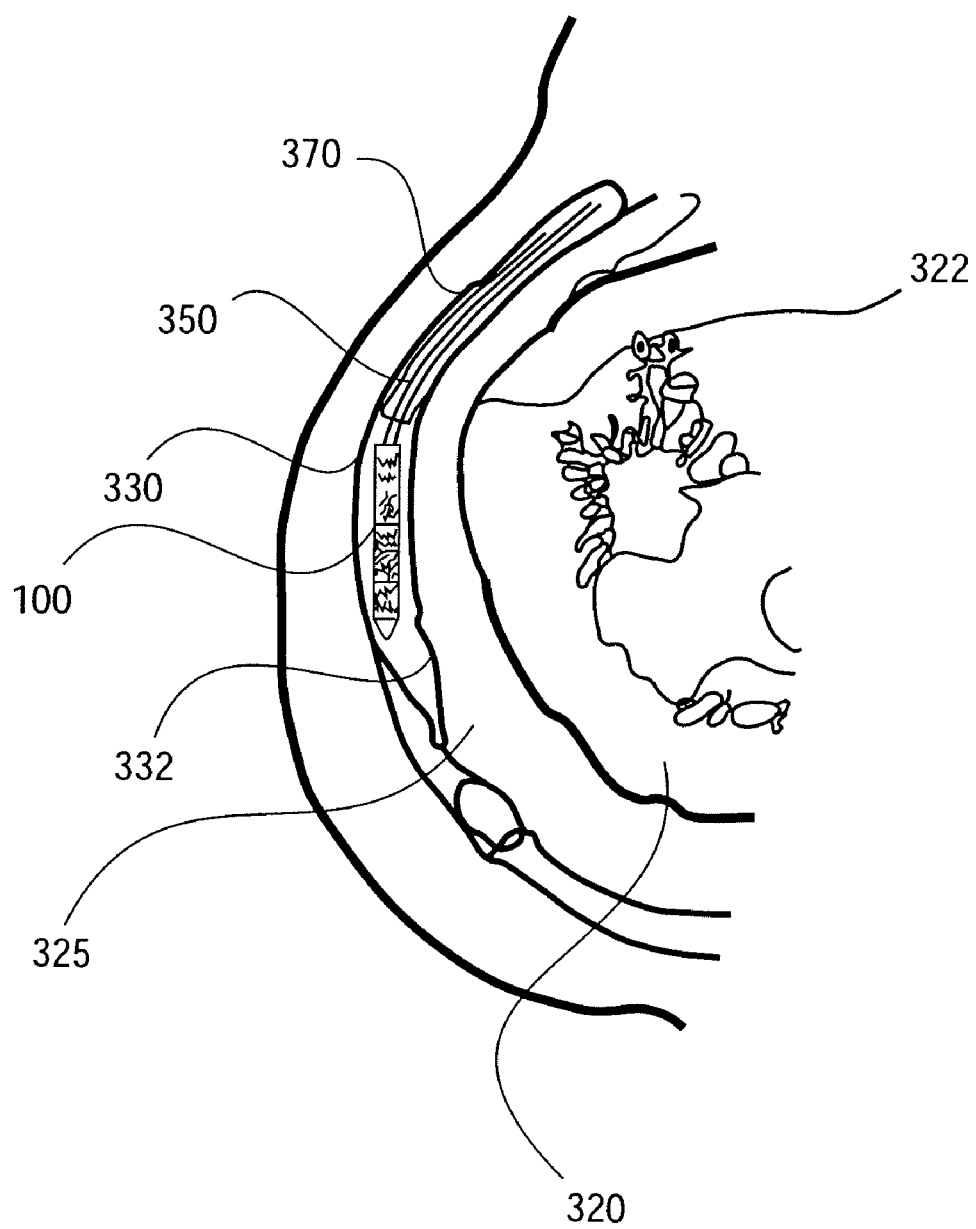
FIG. 24 is an illustration of an embodiment of an unexpanded segmented stent placed in the circumflex branch of the heart.

FIG. 24 is an illustration of an embodiment of unexpanded stent 100 disposed in a body lumen near a valve annulus (e.g., circumflex branch 330, coronary sinus, coronary artery). Unexpanded stent 100 may be delivered to the body vessel by various delivery methods. For example, the stent may be delivered to a desired location within the patient's body by mounting the stent on an expandable member, such as a balloon catheter, provided on a distal end of an intravascular catheter and a sheath extending, for example, from a proximal end of the catheter over the stent. A guide catheter may be routed through a femoral artery into the aorta and into, for example, the circumflex branch of the left main coronary artery, possibly with the aid of a guide wire. The intravascular catheter including the stent may then be advanced through the guide catheter and positioned at a desired location with, for example, a suitable visualization technique. The exterior sheath may be retracted to expose the stent. FIG. 24 shows stent 100 mounted on intravascular catheter 350 and positioned within circumflex branch 330.

To place a stent (such as stent 100) in the coronary sinus from a femoral artery, a guide catheter and possibly a guide wire may first be introduced through the inferior vena cava and into the right atrium. One exemplary guide catheter for delivering a stent to a desired location within, for example, a coronary sinus, is described in a commonly-assigned U.S. patent application Ser. No. 10/293,535, filed Nov. 12, 2002 to Eric T. Johnson and Cindy Sherman, entitled "Guide Catheter," which is hereby incorporated by reference.

According to one aspect, the stent inserted into a body lumen near a mitral valve annulus or tricuspid valve annulus serves to support and/or constrict a surface of a valve annulus of an antrioventricular valve. In one embodiment, the stent may be inserted in the coronary sinus or the circumflex artery or both to inhibit an annulus surrounding the mitral valve from lengthening. In another embodiment, certain segments of the inserted stent are capable of shrinking in length as they are radially expanded so that the stent can be used to constrict a surface of a body lumen near an antrioventricular valve annulus so as to reshape the valve annulus. When an antrioventricular valve such as a mitral or tricuspid valve fails to close completely, the segmented stent may be used to constrict a surface of a body lumen near the valve annulus so as to cause the heart valve to close properly and to reduce the severity of regurgitation during ventricular contraction.

Figure 25:
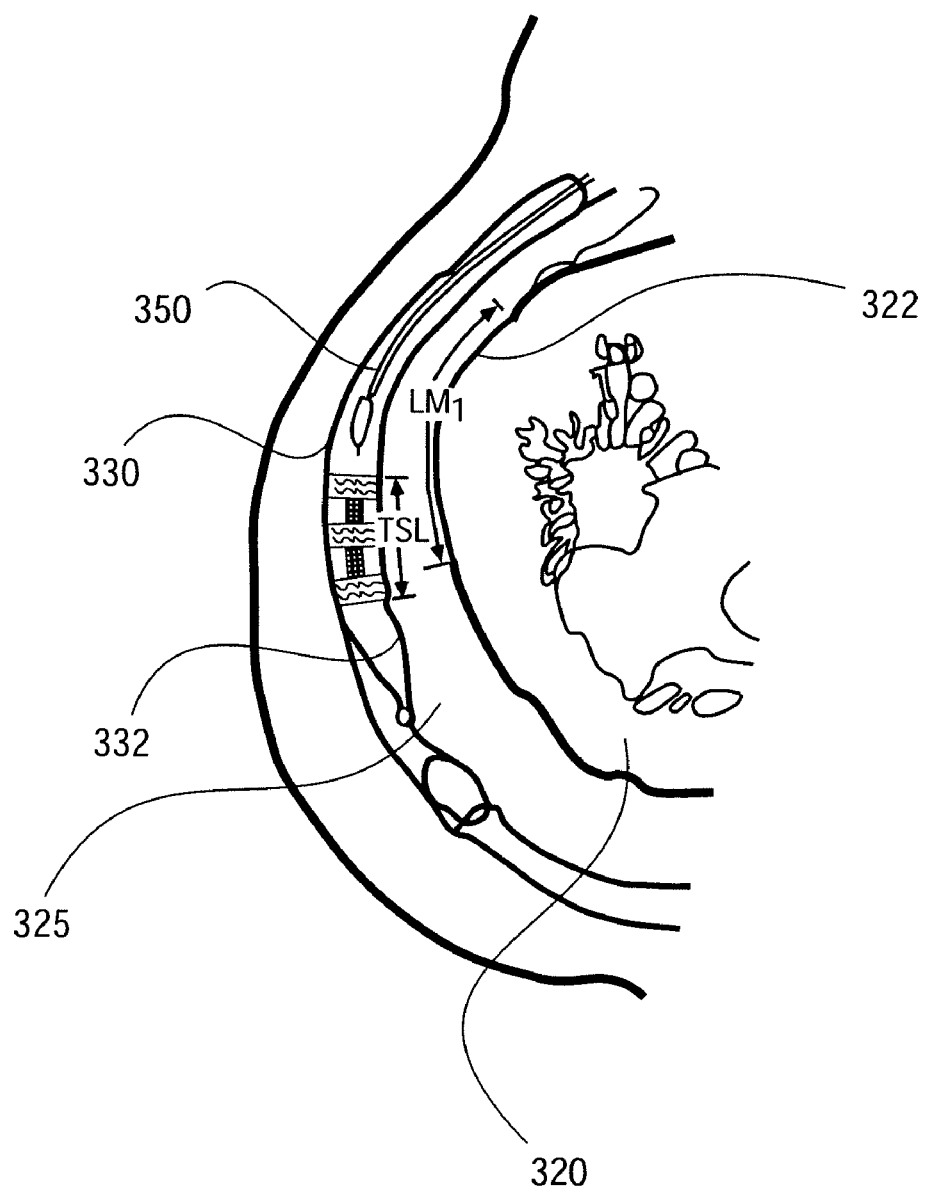
FIG. 25 is an illustration of an embodiment of a segmented stent placed in the circumflex branch of the heart with a first group of segments expanded.

FIG. 25 is an illustration of an embodiment of stent 100 after portions of the segmented stent are securely attached to an interior wall of circumflex branch 330. In one embodiment, this is accomplished by inflating certain segments of a catheter balloon once the stent has been inserted into a desired location so as to expand radial traction segments against the interior wall (see, e.g., FIGS. 5-6 and the accompanying text). Alternatively, the segments are secured one at a time with a balloon catheter having a single balloon (e.g., by positioning the balloon within a radial segment, inflating, deploying, then repositioning). When the radial fraction segments are expanded against the interior wall, hooks 105 on the radial traction segments will become securely seated to the body lumen surface. As described above, when segments 140 are unexpanded, stent 100 has a length $TSL_1$. A second length $LM_1$ is defined as a length of a segment of surface 322 of mitral valve 320 that is generally parallel to the portion of inner surface 332 of circumflex branch 330 which defines $TSL_1$. FIG. 25 shows catheter 35 refracted proximal to stent 100.

Figure 26:
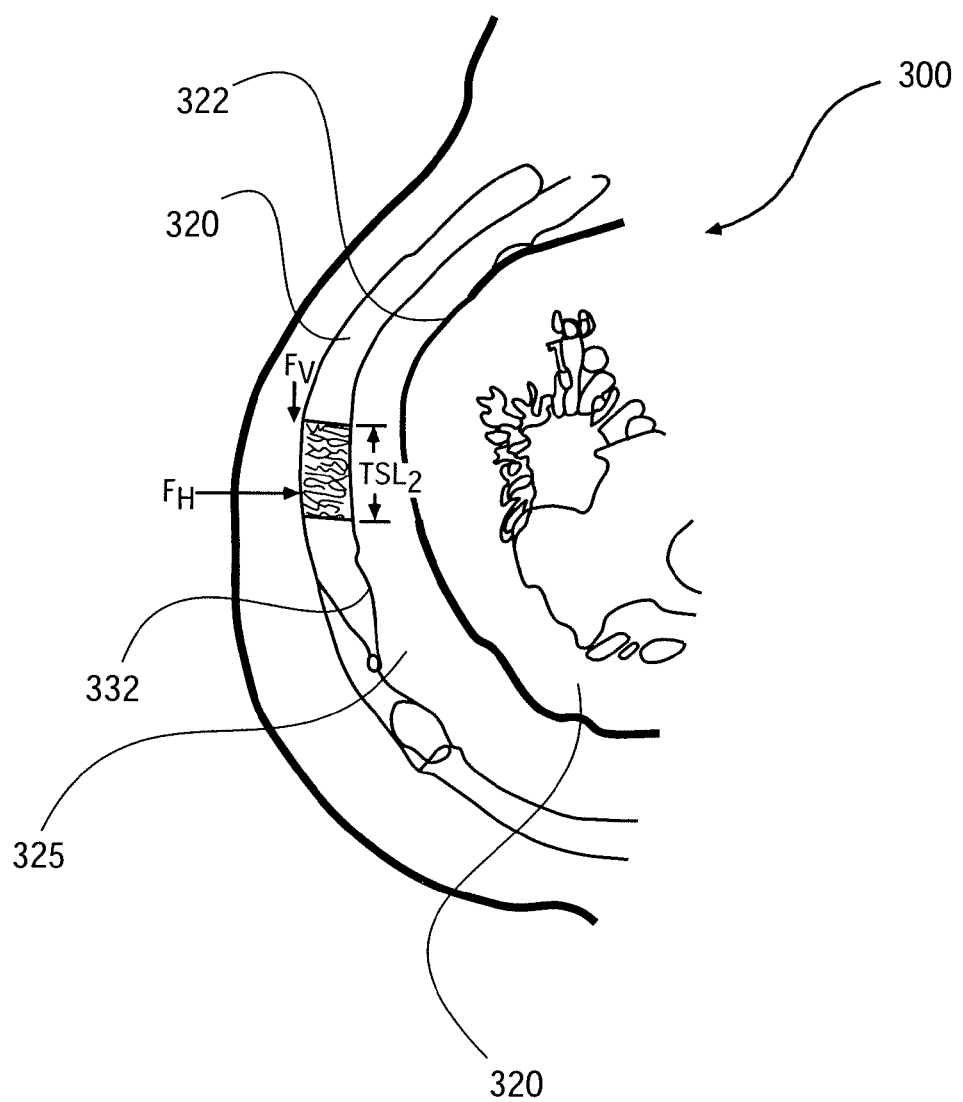
FIG. 26 is an illustration of an embodiment of the stent illustrated in FIG. 25 after shrink segments have been radially expanded.

Once the stent has been securely implanted, certain segments of the catheter balloon may be inflated so as to radially expand one or more of the shrink segments (see, e.g., FIGS. 7-22 and the accompanying text). By doing so, the shrink segments, which shrink in length as they are radially expanded, will pull radial traction segments toward one another. Certain ones of the radial fraction segments that are connected to the inner wall of the circumflex branch 330 (for example, through seated hooks 105) will tend to cause a length of circumflex branch 330 to constrict. The stent 100 illustrated in FIG. 25 after shrink segments 140 have been radially expanded is shown in FIG. 26. Upon expansion of shrink segments 140, the length of shrink segments 140 collectively decrease the length of stent 100 from $TSL_1$ to $TSL_2$. Seated hooks 105 constrict inner surface 332 of circumflex branch 330, as traction segments 110 are pulled together by shrink segments 140. The constriction of inner surface 322 of circumflex branch 320 causes vertical force, $F_V$, and horizontal force, $F_H$, to be applied to surface 322 of mitral valve 330. Forces $F_V$ and $F_H$ result in reinforcement of, and/or indirect constriction of surface 322 of mitral valve annulus 325. According to one aspect, the constriction of the surface of an atrioventricular valve annulus reshapes the valve annulus so that the valve (e.g., mitral valve) closes properly and reduces regurgitation. As such, regurgitation may be reduced without annuloplasty.

In one embodiment, each shrink segment of the segmented stent is configured to be reduced in length over a range of longitudinal length, as it is radially expanded. This allows the overall stent length to be selectively adjusted over a defined ranged of longitudinal length. Accordingly, an operator (e.g., physician) may readjust the longitudinal length of the stent, after the initial insertion, if additional constricting of an annulus surrounding a heart valve is required. For example, a balloon catheter (e.g., a multi-lumen balloon catheter) may be reinserted into a patient and positioned within stent 100. Visualization techniques may be used to properly position the balloon. Representatively, visualization markers (e.g., radiopaque markers) may be present on stent 100 or the balloon segments of a balloon catheter or both. Once positioned, selected shrink segments may be modified to constrict/expand a blood vessel (e.g., circumflex branch 330) to reshape an antrioventricular valve annulus.

FIGS. 24 to 26 illustrate a stent structure (stent 100) placed in a circumflex branch of the left coronary artery. It is appreciated that a similar structure may alternatively or additionally placed in the coronary sinus adjacent a portion of the mitral valve annulus. It is also appreciated that the stent or method described may be used in a variety of body lumens or vessels, not just those adjacent atrioventricular valve annulus, to support or constrict the body lumen or structures adjacent the body lumen.

While the foregoing embodiments have been described and shown, it is understood that variations and modifications, such as those suggested and others within the spirit and scope of the following claims, may occur to those skilled in the art to which the invention pertains.

What is claimed is:

1. A method comprising:
attaching an implantable device in a blood vessel; and
after attaching, constricting a valve annulus near the blood vessel by shortening a length of the implantable device in the blood vessel, wherein the implantable device comprises a tubular device having at least two shrink segments, each shrink segment disposed between a different pair of at least three attachable portions attached to the blood vessel, wherein shortening the length comprises expanding the at least two shrink segments, and wherein each of the two shrink segment that is expanded is individually expanded by a different corresponding segment of a balloon by expanding each different corresponding segment of the balloon using a separate lumen, wherein expanding comprises gradually shortening the length of the implantable device by first expanding a shrink segment adjacent to an already attached attachable portion at an end of the implantable device, and then expanding a second shrink segment later.

2. The method of claim 1, wherein at least one shrink segment is not expanded.

3. The method of claim 1, wherein a plurality of shrink segments are separated from one another by another segment.

4. The method of claim 1, further comprising individually expanding a first shrink segment by only inflating a first segment of the balloon using a first lumen; and then subsequently individually expanding a different second shirk segment by only inflating a different second balloon using a different second lumen.

5. The method of claim 1, wherein expanding comprises gradually shortening the length of the implantable device over a period of time by expanding a first shrink segment at one time, and then expanding a second shrink segment at least one month later.

6. A method comprising:
inserting a tubular member into a body vessel, the tubular member having at least three attachable portions and a different plurality of expandable segments, each expandable segment disposed between a different pair of attachable portions;
attaching the attachable portions of the tubular member to an interior wall of the body vessel;
after attaching, drawing a first and second of the attachable portions towards each other by selectively radially partially expanding only a first one, but not a second one of the plurality of expandable segments, and then, later, further expanding the first one of the plurality of expandable segments to gradually reduce the length of the first one of the plurality of expandable segments, wherein the first one of the plurality of expandable segments is adjacent to an already attached attachable portion at an end of the tubular member; and then
drawing the second and a third of the attachable portions towards each other by selectively radially expanding the second one, but not the first one of the plurality of expandable segments.

7. The method of claim 6, wherein the tubular member attached to the body vessel prevents a portion of the body vessel from increasing in length.

8. The method of claim 6, further comprising coating the tubular member with a drug to treat valve regurgitation.

9. The method of claim 6, wherein the tubular member is placed in a coronary sinus.

10. The method of claim 6, wherein the tubular member is placed in a circumflex artery.

11. The method of claim 6, wherein the tubular member is placed in a right coronary artery.

12. The method of claim 6, further comprising tightening an annulus surrounding a mitral heart valve by reducing a longitudinal length of the attached tubular member.

13. The method of claim 6, further comprising tightening an annulus surrounding a tricuspid heart valve by reducing a longitudinal length of the attached tubular member.

14. The method of claim 6, wherein the tubular member comprises at least two traction segments having a plurality of hooks, said traction segments expandable to seat the plurality of hooks in the body vessel.

15. The method of claim 14, wherein the tubular member further comprises at least one shrink segment coupled between the traction segments, said at least one shrink segment capable of decreasing in longitudinal length to draw one of the traction segments towards the other traction segment.

16. The method of claim 15, wherein the drawing one of the traction segment towards the other traction segment comprises expanding the shrink segment in a radial direction.

17. The method of claim 15, further comprising adjusting a longitudinal length of the tubular member by selectively expanding the shrink segment in a radial direction.

18. The method of claim 6, further comprising selectively expanding at least one segment of the tubular member without expanding other segments of the tubular member.

19. The method of claim 6, wherein at least one of the plurality of expandable segments is not expanded.

20. The method of claim 6, wherein at least one of the plurality of expandable segments is radially expanded at a different time than another of the plurality of expandable segments.

21. The method of claim 6, wherein each of the plurality of expandable segments are separated from one another by another segment.

22. The method of claim 6, wherein radially expanding only the first one, but not the second one of expandable segments comprises expanding a first balloon segment of a balloon using a first lumen, but not expanding a second balloon segment of the balloon; and wherein expanding only the second one, but not the first one of the plurality of expandable segments comprises individually expanding a second balloon segment of the balloon using a second lumen, without further expanding the first balloon segment.

23. The method of claim 6, further comprising:
individually expanding only the first of the expandable segments by inflating an inflatable segment of a balloon;
deflating the inflatable segment of the balloon;
realigning the inflatable segment with the second of the expandable segments; and
individually expanding the second segment by inflating the inflatable segment of the balloon.

24. The method of claim 6, wherein further expanding comprises further expanding at least one month later.

25. A method comprising:
attaching an implantable device in a blood vessel; and
after attaching, constricting a valve annulus near the blood vessel by shortening a length of the implantable device in the blood vessel, wherein the implantable device comprises a tubular device having at least two shrink segments, each shrink segment disposed between a different pair of at least three attachable portions attached to the blood vessel, wherein shortening the length comprises expanding the at least two shrink segments, and wherein each of the two shrink segment that is expanded is individually expanded by a different corresponding segment of a balloon by expanding each different corresponding segment of the balloon using a separate lumen, wherein expanding comprises first expanding a shrink segment adjacent to an already attached attachable portion at an end of the implantable device, wherein at least one shrink segment is expanded at a different time and by a different amount than another of the plurality of expandable segments.

26. A method comprising:
inserting a tubular member into a body vessel, the tubular member having at least three attachable portions and a different plurality of expandable segments, each expandable segment disposed between a different pair of attachable portions;

attaching the attachable portions of the tubular member to an interior wall of the body vessel;

after attaching, drawing a first and second of the attachable portions towards each other by selectively radially partially expanding only a first one, but not a second one of the plurality of expandable segments by inflating an inflatable segment of a balloon, and then, later, further expanding the first one of the plurality of expandable segments by inflating an inflatable segment of a balloon to gradually reduce the length of the first one of the expandable segments, wherein the first one of the plurality of expandable segments is adjacent to an already attached attachable portion at an end of the tubular member; and then drawing the second and a third of the attachable portions towards each other by selectively radially expanding the second one, but not the first one of the plurality of expandable segments by:

deflating the inflatable segment of the balloon;

realigning the inflatable segment with the second of the expandable segments; and individually expanding the second segment by inflating the inflatable segment of the balloon, wherein expanding a first balloon segment of a balloon using a first lumen comprises partially expanding the first balloon, and then further expanding the first balloon to gradually reduce the length of the first one of the expandable segments.

27. A method comprising:

inserting a tubular member into a body vessel, the tubular member having at least three attachable portions and a different plurality of expandable segments, each expandable segment disposed between a different pair of attachable portions;

attaching the attachable portions of the tubular member to an interior wall of the body vessel;

after attaching, drawing a first and second of the attachable portions towards each other by selectively radially individually expanding only a first one, but not a second one of the plurality of the expandable segments by inflating an inflatable segment of a balloon, wherein individually expanding only the first of the expandable segments comprises partially expanding only the first of the expandable segments, and then further expanding the first of the expandable segments to gradually reduce the length of the first of the expandable segments, wherein the first one of the plurality of expandable segments is adjacent to an already attached attachable portion at an end of the tubular member; then drawing the second and a third of the attachable portions towards each other by selectively radially expanding the second one, but not the first one of the plurality of expandable segments by:

deflating the inflatable segment of the balloon; then realigning the inflatable segment with the second of the expandable segments; and then individually expanding the second segment by inflating the inflatable segment of the balloon, wherein individually expanding only the second of the expandable segments comprises partially expanding the only second of the expandable segments, and then further expanding the second of the expandable segments to gradually reduce the length of the second of the expandable segments.

* * * * *